(12) United States Patent
Awdeh

(10) Patent No.: US 10,073,515 B2
(45) Date of Patent: Sep. 11, 2018

(54) SURGICAL NAVIGATION SYSTEM AND METHOD

(71) Applicant: Nanophthalmos, LLC, Miami, FL (US)

(72) Inventor: Richard Awdeh, Miami, FL (US)

(73) Assignee: Nanophthalmos, LLC, Miami, FL (US)

( * ) Notice: Subject to any disclaimer, the term of this patent is extended or adjusted under 35 U.S.C. 154(b) by 586 days.

(21) Appl. No.: 14/488,850

(22) Filed: Sep. 17, 2014

(65) Prior Publication Data

US 2015/0077528 A1 Mar. 19, 2015

Related U.S. Application Data

(60) Provisional application No. 61/879,652, filed on Sep. 18, 2013.

(51) Int. Cl.
*H04N 13/00* (2018.01)
*G06F 3/01* (2006.01)
(Continued)

(52) U.S. Cl.
CPC .............. *G06F 3/012* (2013.01); *A61B 3/005* (2013.01); *A61B 3/0058* (2013.01); *A61B 3/14* (2013.01);
(Continued)

(58) Field of Classification Search
CPC .. G06T 11/00; A61F 9/007; A61F 9/00; G06F 3/012; A61B 34/20; A61B 34/25;
(Continued)

(56) References Cited

U.S. PATENT DOCUMENTS

| | | |
|---|---|---|
| 5,359,417 A | 10/1994 | Muller et al. |
| 7,784,947 B2 | 8/2010 | Pérez et al. |

(Continued)

FOREIGN PATENT DOCUMENTS

| | | |
|---|---|---|
| DE | 102014201571 A1 | 7/2015 |
| EP | 1235094 A2 | 8/2002 |

(Continued)

OTHER PUBLICATIONS

International Search Report and Written Opinion issued in PCT/US2014/056039 dated Sep. 17, 2014 (18 pages).
(Continued)

*Primary Examiner* — Nguyen Truong
(74) *Attorney, Agent, or Firm* — Finnegan, Henderson, Farabow, Garrett & Dunner LLP

(57) ABSTRACT

A surgical guidance system and method for assisting a surgeon in a surgical procedure performed on a patient is disclosed. The system comprises an image acquisition device configured to generate substantially real-time digital video data representing patient images of an eye of the patient. The system further comprises a processor coupled to the image acquisition device and configured to receive the digital video data from the image acquisition device, receive external data from an external data source, and generate composite digital image data based on the digital video data and the external data. The system further comprises a display device coupled to the processor, the display device being configured to display, to the surgeon from the composite digital image data, overlaid images including procedural prompts according to the patient images and the external data.

38 Claims, 29 Drawing Sheets

(51) Int. Cl.
*A61F 9/00* (2006.01)
*G06T 11/00* (2006.01)
*A61B 34/20* (2016.01)
*A61B 34/00* (2016.01)
*A61B 3/00* (2006.01)
*A61B 3/14* (2006.01)
*A61F 9/007* (2006.01)
*A61B 90/50* (2016.01)
*A61B 90/20* (2016.01)
*A61B 90/00* (2016.01)

(52) U.S. Cl.
CPC .............. *A61B 34/20* (2016.02); *A61B 34/25* (2016.02); *A61F 9/00* (2013.01); *G06F 3/011* (2013.01); *G06T 11/00* (2013.01); *A61B 90/20* (2016.02); *A61B 2034/2061* (2016.02); *A61B 2034/252* (2016.02); *A61B 2090/365* (2016.02); *A61B 2090/371* (2016.02); *A61B 2090/372* (2016.02); *A61B 2090/3735* (2016.02); *A61B 2090/502* (2016.02); *A61F 9/007* (2013.01)

(58) Field of Classification Search
CPC ...... A61B 2034/2061; A61B 2034/252; H06F 3/011
USPC ............................... 348/53, 78; 345/156, 634
See application file for complete search history.

(56) References Cited

U.S. PATENT DOCUMENTS

| | | |
|---|---|---|
| 7,800,820 B2 | 9/2010 | Awdeh |
| 7,905,887 B2 | 3/2011 | Moeller et al. |
| 8,414,123 B2 | 4/2013 | Boukhny et al. |
| 8,486,085 B2 | 7/2013 | Moeller et al. |
| 8,708,488 B2 | 4/2014 | Kraus et al. |
| 9,149,340 B2 | 10/2015 | Boukny et al. |
| 2003/0223037 A1 | 12/2003 | Chernyak |
| 2005/0277913 A1 | 12/2005 | McCary |
| 2006/0082542 A1 | 4/2006 | Morita et al. |
| 2006/0247659 A1 | 11/2006 | Moeller et al. |
| 2007/0156019 A1* | 7/2007 | Larkin .................. B25J 19/025 600/104 |
| 2008/0123183 A1 | 5/2008 | Awdeh |
| 2008/0291532 A1 | 11/2008 | Xu et al. |
| 2009/0048608 A1 | 2/2009 | Boukhny et al. |
| 2009/0093798 A1 | 4/2009 | Charles |
| 2009/0209884 A1* | 8/2009 | Van Vorhis ............. G06F 19/34 600/595 |
| 2010/0152847 A1 | 6/2010 | Padrick et al. |
| 2010/0208199 A1* | 8/2010 | Levis ...................... A61B 3/11 351/204 |
| 2011/0019151 A1 | 1/2011 | Schuhrke et al. |
| 2011/0122365 A1 | 5/2011 | Kraus et al. |
| 2011/0257638 A1 | 10/2011 | Boukhny et al. |
| 2011/0292340 A1 | 12/2011 | Shimizu et al. |
| 2012/0197102 A1 | 8/2012 | Hanebuchi et al. |
| 2012/0330129 A1 | 12/2012 | Awdeh |
| 2013/0041226 A1* | 2/2013 | McDowall ......... A61B 1/00009 600/166 |
| 2013/0088414 A1 | 4/2013 | Artsyukhovich et al. |
| 2013/0204236 A1 | 8/2013 | Awdeh |
| 2013/0271845 A1 | 10/2013 | Butler et al. |
| 2014/0039510 A1* | 2/2014 | van Saarloos ......... A61B 3/107 606/107 |

FOREIGN PATENT DOCUMENTS

| | | |
|---|---|---|
| EP | 2184005 A1 | 5/2010 |
| EP | 2322083 A1 | 5/2011 |
| WO | WO 2009/029638 | 3/2009 |

OTHER PUBLICATIONS

European Search Report, dated Jun. 7, 2017, in the European Application No. EP14845155.2, filed on Nov. 4, 2016 by Awdeh.
European Search Report, dated Sep. 19, 2017, in the European Application No. EP15761534.5, filed on Apr. 28, 2017 by Awdeh.
European Search Report, dated Oct. 19, 2017, in the European Application No. EP15760909.0, filed on Apr. 28, 2017 by Awdeh.

* cited by examiner

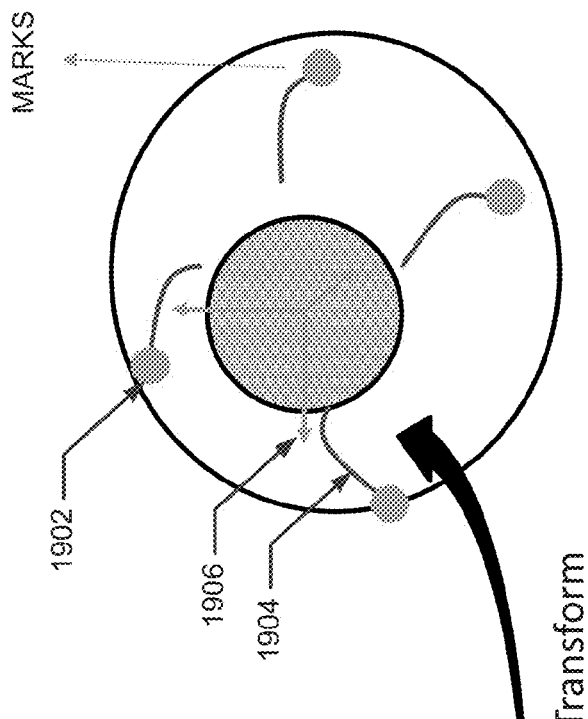

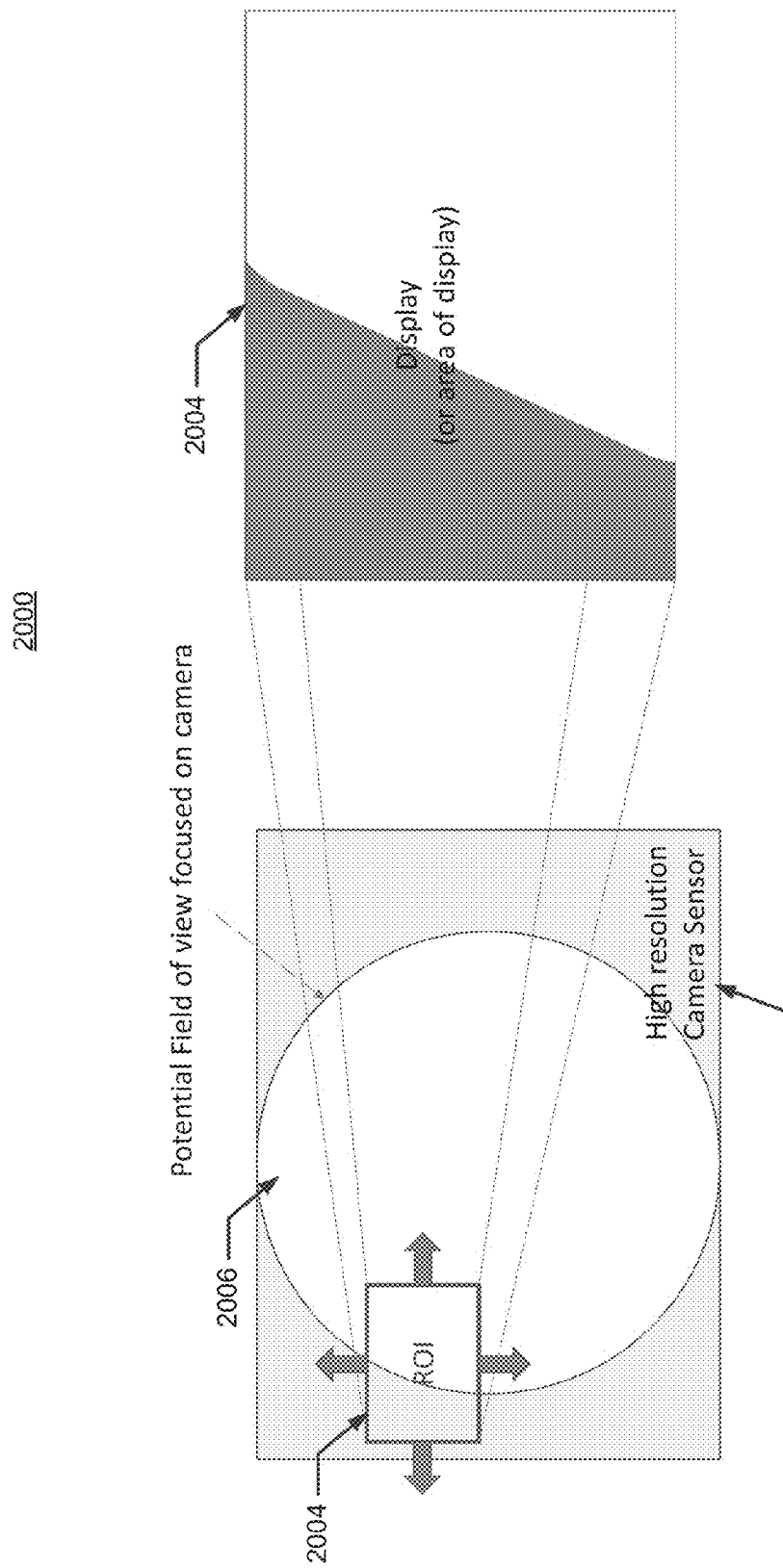

| Resolution | Color Depth | Frame Rate | Required Transfer Rate |
|---|---|---|---|
| 1280 x 720 (720p) | 24-bit | 60 Hz | 1.33 Gbit/sec |
| 1280 x 720 (720p) | 30-bit | 60 Hz | 1.66 Gbit/sec |
| 1280 x 720 (720p) | 36-bit | 60 Hz | 1.99 Gbit/sec |
| 1280 x 720 (720p) | 48-bit | 60 Hz | 2.65 Gbit/sec |
| 1920 x 1080 (1080p) | 24-bit | 60 Hz | 2.98 Gbit/sec |
| 1920 x 1080 (1080p) | 30-bit | 60 Hz | 3.73 Gbit/sec |
| 1920 x 1080 (1080p) | 36-bit | 60 Hz | 4.48 Gbit/sec |
| 1920 x 1080 (1080p) | 48-bit | 60 Hz | 5.97 Gbit/sec |
| 1280 x 720 (720p) | 24-bit | 90 Hz | 1.99 Gbit/sec |
| 1280 x 720 (720p) | 30-bit | 90 Hz | 2.49 Gbit/sec |
| 1280 x 720 (720p) | 36-bit | 90 Hz | 2.99 Gbit/sec |
| 1280 x 720 (720p) | 48-bit | 90 Hz | 3.98 Gbit/sec |
| 1920 x 1080 (1080p) | 24-bit | 90 Hz | 4.48 Gbit/sec |
| 1920 x 1080 (1080p) | 30-bit | 90 Hz | 5.60 Gbit/sec |
| 1920 x 1080 (1080p) | 36-bit | 90 Hz | 6.72 Gbit/sec |
| 1920 x 1080 (1080p) | 48-bit | 90 Hz | 8.96 Gbit/sec |

*FIG. 23*

SURGICAL NAVIGATION SYSTEM AND METHOD

TECHNICAL FIELD

Embodiments of the present disclosure relate to the field of medical devices and, in particular, to devices for surgical visualization and navigation systems.

BACKGROUND

Medical visualization systems, for instance medical microscopes or medical cameras, allow a user, such as a surgeon or other medical staff, to view objects in a light path on which the visualization system is focused. During a procedure, however, a surgeon may need to view multiple images simultaneously, for instance, in side-by-side comparison or superimposed, or may need to keep track of information (e.g., data) located outside of the light path or field of view. For instance, a surgeon may require confirmation of anatomical and/or surgical landmarks, e.g., navigational assistance, or may require confirmation of anatomical locations, e.g., to identify cancer margins during diagnosis or tumor resection. Such information may include real-time or static information, such as other images, e.g., magnetic resonance imaging (MRI), computed tomography (CT), optical coherence tomography (OCT), x-ray, or fluorescien angiography (FA) images, patient data, e.g., vital signs or medical records, and/or operation parameters of one or more medical instruments. The ability to incorporate external data into a surgeon's image space in order to relay data points to the surgeon without the surgeon looking away from the surgical field is of great value. Exemplary visualization systems are described, for instance, in U.S. Pat. No. 7,800,820, granted to the inventor hereof, the entirety of which is incorporated by reference herein. There remains a need, however, for visualization systems capable of incorporating external data into the surgeon's field of vision via, for example, a surgical microscope or eyewear device that a user, such as a surgeon or other medical professional, may use during medical procedures, to help the surgeon to "navigate" through the procedure. Further, there is a need for an improved surgical navigation system capable of incorporating external data points, such as three-dimensional data points and registered anatomical and pathological landmarks, into a surgeon's field of vision for real-time navigational assistance to manipulate surgical instruments into a desired location with respect to a portion of a patient upon which a surgical procedure is being performed.

When viewing an image through a microscope or other similar viewing device, an operator can directly view a real-time, live image located within the light path of the device. This image may appear three-dimensional due to the nature of binocular vision, because the glass viewing lenses are situated directly in front of each eye. Such a viewing arrangement may not be possible when the medical camera or other image capture device is located at a distance from the viewer, for instance, within a patient. In this case, external displays set some distance from the image capture device, such as monitors or medical eyewear, may be utilized. The image capture device may relay information to external processors and/or displays for operator viewing. Such displays are two-dimensional, and an image is created using pixels on the display. Thus, unlike microscopes or more direct viewing devices, the displayed image may not appear three-dimensional. During medical procedures, for instance, an operator may require three-dimensional images to efficiently treat or diagnose a patient. Thus, a need remains for improved systems and methods capable of producing three-dimensional images that may be integrated with external data.

SUMMARY

Consistent with the disclosed embodiments, a surgical guidance system for assisting a surgeon in a surgical procedure performed on a patient is disclosed. The system comprises an image acquisition device configured to generate substantially real-time digital video data representing patient images of an eye of the patient. The system further comprises a processor coupled to the image acquisition device and configured to receive the digital video data from the image acquisition device, receive external data from an external data source, and generate composite digital image data based on the digital video data and the external data. The system further comprises a display device coupled to the processor, the display device being configured to display, to the surgeon from the composite digital image data, overlaid images including procedural prompts according to the patient images and the external data.

Consistent with some other embodiments, a medical data visualization system is disclosed. The system comprises an image acquisition device configured to generate substantially real-time video data representing patient images of a patient corresponding to a field of view. The system further comprises a processor coupled to the image acquisition device and configured to receive the video data from the image acquisition device, receive external data from an external data source, and generate composite digital image data based on the video data and the external data. The system further comprises a display device coupled to the processor, the display device being configured to display overlaid images including a portion of the patient image corresponding to a region of interest and a graphical representation of the external data.

Consistent with some other embodiments, a computer system for assisting a surgeon in a surgical procedure performed on a patient is disclosed. The computer system comprises an input module configured to receive from an image acquisition device, substantially real-time digital video data representing patient images of an eye of the patient, and external data. The system further comprises a processing module configured to generate composite digital image data based on the digital video data and the external data, and an output module configured to transmit the composite digital image data to a display device for display of overlaid images including procedural prompts corresponding to the patient images and the external data.

Consistent with some other embodiments, a display device for assisting a surgeon in a surgical procedure performed on a patient is disclosed. The device comprises a housing configured to be worn by the surgeon, a receiving module, and a display module. The receiving module is configured to receive composite digital image data from a processor including substantially real-time digital video data and external data, the digital video data representing patient images of an eye of the patient. The display module is configured to display, to the surgeon from the composite digital image data, overlaid images including procedural prompts corresponding to the patient images and the external data.

Consistent with some other embodiments, a method for assisting a surgeon in a surgical procedure performed on a patient is disclosed. The method comprises receiving substantially real-time digital video data representing patient images of an eye of the patient, receiving external data from an external data source, generating composite digital image data based on the digital video data and the external data, and transmitting the composite digital image data to a display device for display of overlaid images from the composite digital image dat. The overlaid images include procedural prompts for the surgical procedure corresponding to the patient images and the external data.

Consistent with some other embodiments, a non-transitory computer-readable medium comprising instructions, which, when executed by one or more processors, cause the processors to perform a method for assisting a surgeon in a surgical procedure performed on a patient. The method comprises receiving substantially real-time digital video data representing patient images of an eye of the patient, receiving external data from an external data source, generating composite digital image data based on the digital video data and the external data, and transmitting the composite digital image data to an display device, for display of overlaid images from the composite digital image data. The overlaid images include procedural prompts for the surgical procedure corresponding to the patient images and the external data.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIGS. 19A and 19B illustrate a feature tracking process for tracking features of a patient, according to an embodiment;

FIGS. 20A and 20B illustrate a process for adjusting a region of interest over an overlaid image display by the system of FIG. 1, according to an embodiment;

FIG. 23 illustrates a transfer rate requirement for data transmission within system of FIG. 1, according to an embodiment;

DETAILED DESCRIPTION OF THE EMBODIMENTS

Reference will now be made in detail to the exemplary embodiments of the present disclosure described below and illustrated in the accompanying drawing. Wherever possible, the same reference numbers will be used throughout to refer to same or like parts.

While the present invention is described herein with reference to illustrative embodiments for particular applications, it should be understood that the invention is not limited thereto. Those having ordinary skill in the art and access to the teachings provided herein will recognize additional modifications, applications, embodiments, and substitution of equivalents, that all fall within the scope of the disclosure. Accordingly, the disclosure is not to be considered as limited by the foregoing or following descriptions.

Figure 1:
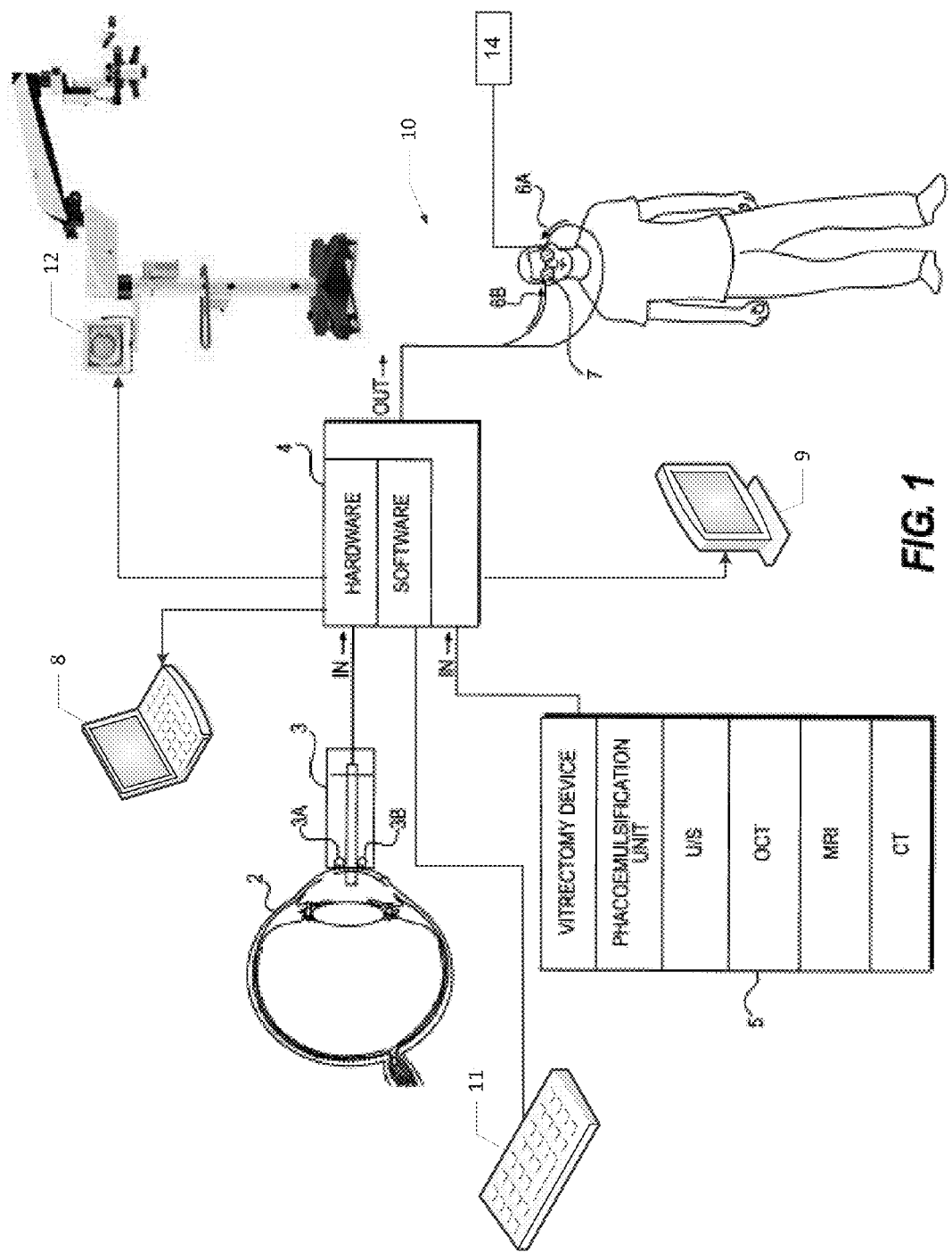
FIG. 1 shows a schematic diagram of a surgical navigation system, according to an embodiment.

FIG. 1 illustrates a surgical visualization and navigation system 10, according to an exemplary embodiment. System 10 may include an image source 3 including one or more image acquisition devices, such as cameras, optical coherence tomography (OCT) devices, or other types of optical sensors. Image source 3 may generate still images, moving images, or video data. In one embodiment, for instance, image source 3 may include two cameras, 3a, 3b. The cameras may be arranged in slightly offset position to provide a stereoscopic view of a surgical field. Cameras 3a, 3b may include any suitable type of camera, e.g., cameras for generating still or moving images, infrared or heat-sensitive cameras, low-light cameras, or the like. System 10 may also include any suitable component for visualization and/or imaging, e.g., one or more light sources, sensors, ultrasound sources, or suction/irrigation sources to clear the surgical field, for instance.

Image source 3 may be coupled to an external organ or inserted into a portion of the human body, such as, an eye 2 (e.g., through the sclera and into the anterior chamber or vitreous space). In particular, certain embodiments of the present disclosure may be used in, or prior to, ophthalmologic surgeries, including vitreo-retinal surgery (e.g., with phacoemulsification, ultrasound, vacuum, aspiration, or irrigation), corrective surgery (e.g., Laser-Assisted in Situ Keratomileusis, or LASIK, and photorefractive keratectomy, or PRK), cataract surgery, astigmatism surgery, glaucoma surgery, or in any other suitable procedures in any other subspecialties, for instance, other surgical fields or dentistry.

System 10 may further include a display device, such as an eye wear device 7, an external display 9, or a microscopic unit 12, configured to receive data from processing unit 4 and display a representation of the data to the surgeon. Eyewear device 7 may include eyeglasses, spectacles, goggles, a helmet, visors, monocles, or any other suitable wearable viewing device. Eyewear device 7 may be operably connected to image source 3 so that images from the cameras are displayed in eyewear device 7 to provide visualization of a surgical field, for instance, to a surgeon. Eyewear device 7 may be physically connected (e.g., via cords, cables, wires, or the like) or wirelessly connected to image source 3 via a processing unit 4, described further below. Eyewear device 7 may include one or more displays for displaying the images from image source 3. The displays may be, e.g., liquid crystal displays (LCDs) or light-emitting diode (LED) displays, and may include, for instance, one or more of an organic light-emitting diode (OLED), a transparent organic light-emitting diode (TOLED), or any other suitable light source. In an embodiment, eyewear device 7 may be a zSight head-mounted display manufactured by Sensics, Inc., 7125 Thomas Edison Dr, Suite 103, Columbia, Md. 21046, USA. Furthermore, eyewear device 7 may, for instance, include any suitable OLED display and/or control systems, such as those manufactured by eMagin Corporation, 3006 Northup Way, Suite 103, Bellevue, Wash. 98004.

Alternatively, the display device may employ a surgical microscope to simultaneously display real-time images of the surgical field overlaid and registered with images of informational and navigational aids. The surgical microscope could comprise a binary optical microscope with a digital display to overlay images of informational and navigational aids using an optical combiner. Alternatively, the microscope could comprise one or more purely digital displays, similar to an electronic viewfinder in a digital camera, to digitally combine image signals of the magnified surgical field and of informational and navigational aids, and display a composite digital image or a pair of composite images to provide three-dimensional viewing.

The one or more displays may be located in each of the eyewear oculars. In one embodiment, each display may have its own video stream 6a, 6b, which may allow for the delivery of data or an image (still, video, or both) signal to each ocular, as discussed further below. Alternatively, each display may share one or more video feeds 6a, 6b. In another embodiment, the display device, such as the eyewear device 7, the external display 9, or the microscopic unit 12, may only have one display and/or one ocular. The display may be transparent, semi-transparent, translucent, or semi-translucent, so that the display image is included in what the surgeon can see through the oculars; or, the oculars can be opaque or semi-opaque, such that the display image is the only image the surgeon can see. In some embodiments, the display device may include controls configured to allow the surgeon to adjust the image displayed on one or both oculars. For instance, the surgeon may be able to zoom in or out of an image, adjust the brightness, contrast, color, or magnification, or completely turn off the display in one or both oculars. This may allow the surgeon to view the image displayed on, e.g., one ocular, while keeping an eye on something else, for instance, when reaching for an instrument or viewing another region of the patient.

System 10 may be configured to incorporate both imaging data from image source 3 and external data, from, for instance, an external data source 5, into the visual field of the surgeon. Any external data that may assist a medical professional during a medical procedure may be included on the display device. Such external data may include real-time or static information, such as other images, e.g., magnetic resonance imaging (MRI), computed tomography (CT), optical coherence tomography (OTC), x-ray, or fluorescein angiography (FA) images; patient data, e.g., physiological parameters or medical records; and/or parameters of or information particular to one or more medical instruments being used, e.g., phacoemulsification machines for cataract surgery, surgical lasers for eye surgery, specifically femtosecond and excimer laser devices, or thermocautery devices.

Processing unit 4 may include one or more processors and a memory. The memory may store instructions, which may be retrieved and executed by the processors. The instructions may cause the processors to perform the processes described herein in connection with the processing and display of the image data from image source 3 and the external data from external data source 5.

Processing unit 4 may acquire data wirelessly or via a physical connection from one or more image sources 3 and/or from one or more external data sources 5 (MRI, CT, ophthalmology/phacoemulsification data stream, medical instruments, patient monitors, cameras, etc.) and may incorporate this data onto the video source data, forming a merged image, for instance, by superimposing the data or arranging the data into discrete images adjacent to each other. In addition to the view of the, e.g., surgical field, provided by image source 3, one or more data images may be produced in the view provided to the display device, thus permitting the surgeon to simultaneously view both the object(s) on which the camera(s) is trained, as well as external data. The external data can include, for instance, vacuum pressure, distance to an object or anatomical landmark, or other suitable information. Still other information could include, for example, the remaining battery life of eyewear device 7 or the time or length of the current operation.

The one or more displays in the display device may receive either merged or unmerged data from processing unit 4. For instance, live video images from cameras 3a, 3b may be displayed by the display device or images from 3a, 3b may be merged in processing unit 4 to form one, merged image for display on the display device. In one embodiment, cameras 3a, 3b may be offset by a pre-specified number of degrees to create a three-dimensional or stereoscopic image on the display device. The images acquired from image source 3 may further include data, such as images or values, from external data source 5 (e.g., a medical device such as an MRI scan, ultrasound machine, vacuum, etc.).

As alluded to above, each set of images or information from external data source 5, image source 3, and/or system 10 may be processed, compiled, and repositioned in processing unit 4. The combined image may then be delivered to the display device. For instance, the image received from image source 3 may include an image representation of an object under study or operation, surrounded by a peripheral region that includes either no image data or background image data. In one embodiment, the external data from external data source 5 may be added to the visual field in this peripheral region on the images from image source 3. In other embodiments, processing unit 4 may superimpose or overlay the external data onto the view of the surgical field from image source 3. The external data may be placed in the peripheral region of the images generated by the display device, while the object under study or operation being displayed to the operator at the central region of the images. In one embodiment, the external data may be delivered to just one ocular, while the other ocular may receive a continuous feed from image source 3. In another embodiment, data from external data source 5 may be delivered to both oculars and may be superimposed over the image from image source 3 in both oculars. This embodiment may be used, for instance, to superimpose a flourescien angiogram of blood vessels over the real-time image of blood vessels during retina surgery or any other suitable procedure. Additional exemplary configurations of the images displayed by each ocular of the eyewear are described in reference to the microscope system in U.S. Pat. No. 7,800,820, for example.

Processing unit 4 may merge data received from both image source 3 and external data source 5 into a left hybrid image and a right hybrid image. The composite display image, including the processed and repositioned images from image source 3 and any other information, may then be sent to the display device. In one embodiment, external data source 5 may include a sensor located on one or more medical instruments configured to transmit orientation information to processing unit 4. Such orientation information may aid processing unit 4 to align and/or orient the images received from image source 3. Alternatively, the orientation information could simply be displayed on the display device to indicate the orientation of the field of view to the surgeon.

In one embodiment, the display device, such as eyewear device 7, may include left and right displays or oculars in communication with processing unit 4. The display device may be configured to display the left hybrid image on the left display and the right hybrid image on the right display. For instance, two data streams 6a, 6b may operably connect processing unit 4 and the display device. A left data stream 6a may provide the left hybrid image from processing unit 4 on the left display of the display device, and the right data stream 6b may provide the right hybrid image from processing unit 4 on the right display device. In another embodiment, external or video source data and/or images may be displayed on one display, while the other display may allow a surgeon to see through. While two video streams 6a, 6b are shown in the exemplary figure, any number of video streams may be used. The images may be sent using any suitable video format, such as, for example, digital, 12-bit video, NTSC, PAL, SECAM, or stereoscopic video.

Processing unit 4 may further include memory for storing external data, images from image source 3, and/or the final composite images sent to the display device. Processing unit 4 may allow the surgeon or an operator to record these images, pause the images, re-orient the images, or otherwise control the images displayed either in real-time or after the images have been recorded. Further, the raw data from image source 3 and external data source 5, and the composite images may be transmitted to an external processor 8 and/or a display monitor 9, located either in the same room or in a remote area. For instance, images may be transmitted to external monitor 9 to allow people other than the surgeon using eyewear device 7 to view the images. The images may also be transmitted to external processor 8 for further processing or storage therein.

According to another embodiment, processing unit 4 may further transmit the patient images, the external data, and/or the composite image data to a microscopic unit 12. Microscopic unit 12 may be a digital or analog unit that allows the surgeon to view the surgical field through a lens system disposed therein. The microscopic unit 12 may receive the data from processing unit 4 and overlay a representation of the external data over the patient image within the field of view of the lens system.

While FIG. 1 depicts processing unit 4 as separate from the display device, processing unit 4 may also be included in the display device. In this embodiment, data from image source 3 and/or external data source 5 may stream directly to the display device, and all remaining processing may be performed by the display device. In other embodiments, some data processing may occur in a processing unit 4 located external from the display device, while some processing may occur within a processing unit 4 located within the display device. In another embodiment, system 10 may include input devices 11, such as a keyboard, a mouse, a touchpad, a touchscreen, a push button panel, etc., to allow the surgeon or other users to control processing unit 4 and the display device. The operator may input data, such as patient identification, pre-operative measurements, patient history, etc., to processing unit 4. The operator-input data may also be merged with image data from image source 3 to form the composite image data and displayed to the operator by the display device in the overlaid images.

In certain embodiments, a surgeon using system 10 may be able to adjust controls on the display device, such as eyewear device 7 or on input device 11 to view only data from image source 3 or to view only data from external data source 5 on the display device, alternatively, or to view external data in one display and image data in the other, or to stop the display of data from all sources. In one embodiment, the physical organization of the display device may allow a surgeon to adjust the data displayed. For instance, the display device may include an outer display portion and an inner display portion. The display device may be configured such that external data is displayed on one of the inner or the outer display portions, and images from image source 3 are displayed on the other of the inner or outer display portion. For instance, the external data may be displayed on the outer portion, and images from image source 3 may be displayed on the internal portion. The outer portion may be configured so that the surgeon may move the outer portion in relation to the inner portion, altering the orientation of the displayed external data relative to the displayed images from image source 3. For instance, in one embodiment, an outer display portion may be, e.g., slidingly, pivotably, or hingedly coupled to the inner portion such that the surgeon may view both the external data and data from image source 3, or alternatively, position the outer portion of the display device such that only one of either the internal or external data can be viewed by the surgeon. In another embodiment, both the outer portion and the inner portion may be movable, or the external data and internal data from image source 3 may both be displayed on the outer portion.

In this embodiment, the surgeon may be able to move the displayed images into and out of the visual field. This may allow the surgeon to alternatively navigate the surrounding environment of the operating room and view the surgical area and/or external data without having to look away from the display device or remove eyewear device 7.

Additionally, the display device, such as eyewear device 7, may be sized and/or shaped so as to allow the surgeon to quickly glance outside of the ocular and/or display region, for instance, to glance just below the display, and view the immediate field through the display device. Alternatively, in one embodiment, the display device may have multiple oculars and/or displays arranged in rows or columns that are configured to display different external data or data from different external data sources 5 to allow the surgeon to glance between each. The displays of this embodiment may be arranged in a manner similar to bifocals, for instance.

Eyewear device 7 may eliminate the need for a microscope in an operating room. Microscopes are ordinarily necessary for many fine procedures, including eye surgeries, and more specifically, for those procedures involving lasers. The ability to use eyewear device 7 instead of a microscope for such procedures may decrease the cost of maintaining medical facilities, which may allow operators to perform these procedures in non-hospital environments, such as clinics. Further, eyewear device 7 may provide a lightweight, portable alternative to traditional medical visualization and navigation systems. This may allow an operator greater freedom of movement. For instance, system 10 may allow on operator to be in a remote location, for instance, in another room, in the case of robotic surgery. Additionally, a plurality of eyewear devices 7 or other display devices may be connected to processing unit 4, which may allow multiple operators and/or multiple observers in any location to view the combined images.

Further, system 10 may enhance the surgeon's ability to perform procedures. In one embodiment, system 10 may include filtering, or other image optimization capabilities, that makes it easier for the surgeon to view certain structures while operating. For instance, a blue filter function may allow an operator to more easily view sutures, for instance, e.g., 10-0 nylon sutures. In another embodiment, system 10 may include processing that provides the image optimization effects digitally and that allows for real-time 'matching' or recognition of anatomical landmarks for navigational assistance. For instance, images from video source 3 may be compared with external data, e.g., with the pre-operative MRI/data studies of anatomical landmarks in the field, and the display shown on system 10 may 'recognize' and indicate these landmarks for an operator. In another embodiment, processing unit 4 may include anatomical maps or anatomical reference images. Algorithms may allow processing unit 4 to compare data from image source 3 with these anatomical maps, and system 10 may indicate certain landmarks or abnormalities in the surgical field to the surgeon, for instance, through visual or auditory signals.

In another embodiment, system 10 may be used in procedures utilizing a contrast agent that is bound to an antibody, or any suitable biomarker, e.g., in procedures involving cancer. In this embodiment, system 10 may include filters either mechanically or digitally configured for use with contrast agents, or may have multiplexing abilities to allow for the use of multiple contrast agents. The filters, e.g., may correspond to the biomarkers used such that system 10 may allow the surgeon to distinguish tumor sections bound by the biomarkers from unbound, non-tumor areas (i.e., to see the 'tumor margins') on the image display to permit the surgeon to perform more exact diagnoses or surgical excisions, for instance.

Exemplary use of such biomarkers is described in, for example, PCT Patent Publication No. WO 2010/148298, of which the inventor hereof is a co-inventor, and the entirety of which is incorporated by reference herein. As disclosed in the PCT application, contrast agents may be used with optical coherence tomography (OCT) imaging to map anatomies or abnormalities, e.g., of the eye. Accordingly, in one embodiment, an OCT probe, e.g. a fiber optic cable, may be configured for insertion into a patient with image source 3. The OCT probe may be mounted, for example, on a catheter tip or inserted through an introduction sheath, such as an endoscope or trocar. Alternatively, the OCT probe may be mounted on the elongated device on which cameras 3a, 3b may be mounted. The OCT probe may act as an external data source 5 and may transmit images to processing unit 4 and eyewear device 7. Processing unit 4 may merge the images from image source 3 and the OCT probe so that the OCT images are superimposed on the surgical field as displayed in eyewear device 7. A three-dimensional image with OCT mapping may be generated and streamed to the display device. This may offer the surgeon OCT image guidance, which may further be multiplexed to contrast agents that are bound to areas within a patient.

Figure 2:
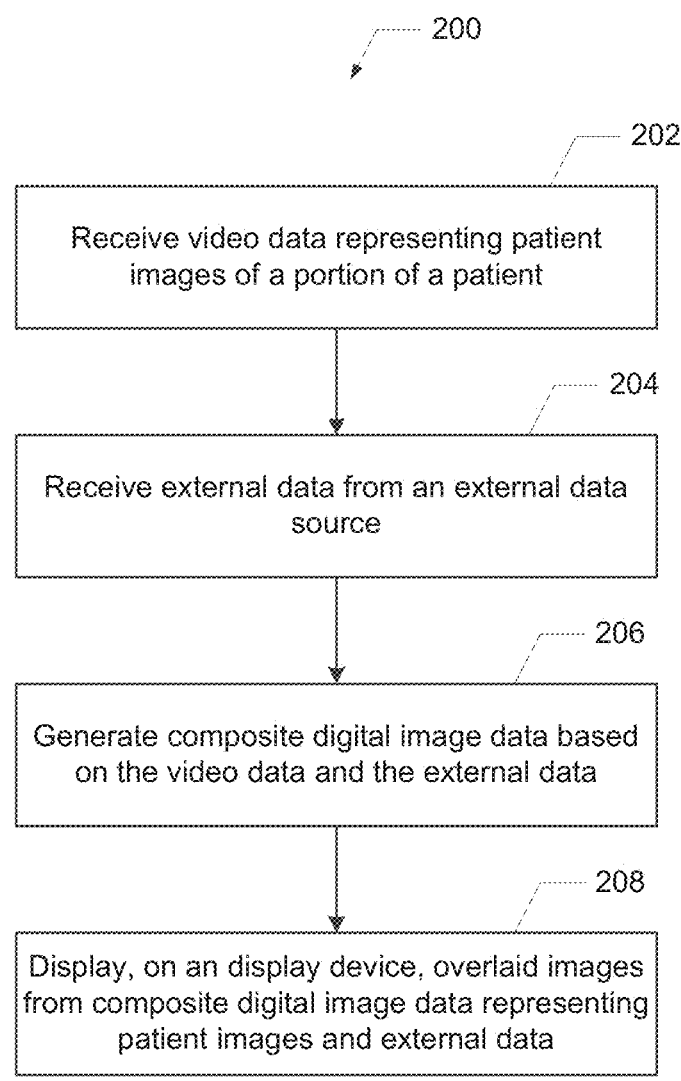
FIG. 2 shows a process for carrying out a surgical procedure using a surgical navigation system, according to an embodiment.
Figure 3:
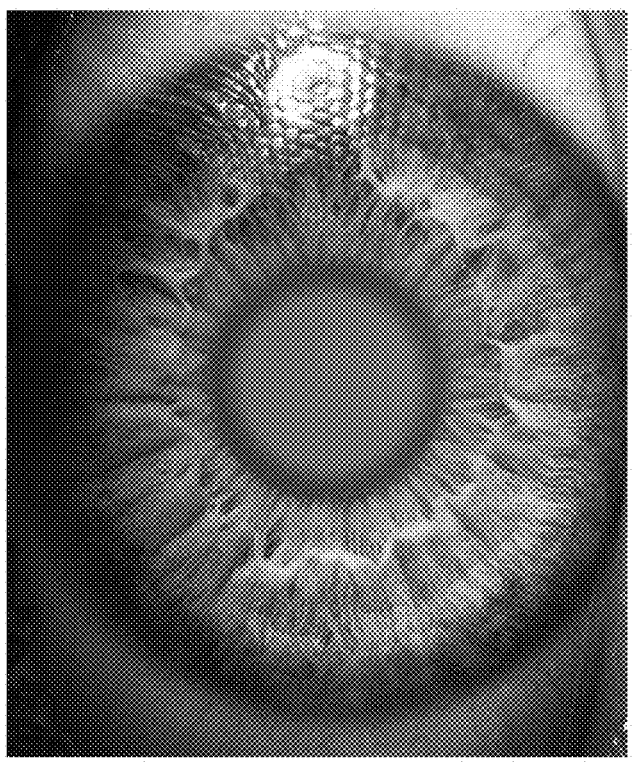
FIG. 3 shows an exemplary digital image of an eye of a patient acquired by cameras of FIG. 1, according to an embodiment.

FIG. 2 illustrates an exemplary process 200 for assisting a surgeon in a surgical procedure performed on a patient, according to an embodiment. Process 200 may be implemented by system 10 depicted in FIG. 1 and carried out during the surgical procedure. According to process 200, at step 202, processing unit 4 receives video data from image source 3. The video data represent patient images of a portion of a patient, such as an eye, an oral portion, or any other internal or external organs or anatomical features. In one embodiment, when image source 3 is attached to the eye of the patient as shown in FIG. 1, the video data represents images of the patient's eye, including ocular structures, such as cornea, iris, pupil, lens, etc. In another embodiment, the video data includes a sequence of digital images. The images have a size generally corresponding to the field of the view of image source 3 including the area under surgery or operation. FIG. 3 illustrates an exemplary patient image included in the video data received from image source 3.

In a further embodiment, the video data representing the patient images are transmitted from image source 3 to processing unit 4. The transmission may be through wired or wireless channels such as a local area network (LAN), a wide area network (WAN), a Wi-Fi network, a Bluetooth link, or any other networks known in the art. Processing unit 4 may store the video data in the memory for later processing. Processing unit 4 may also process the video data according to instructions stored in the memory. For example, processing unit 4 may crop the video data to a specific size, filter the video data to remove undesired image features or noise, enhance the video data to emphasize certain edges or colors, etc.

At step 204, processing unit 4 receives external data from external data source 5. External data source 5 may be any surgical system or monitoring system known in the art. In one embodiment, external data source 5 may include a surgical system such as the Stellaris Micro Incision Cataract Surgery (MICS) system manufactured by Bausch & Lomb, Inc. of One Bausch & Lomb Place Rochester, N.Y. 14604-2701.

Figure 4:
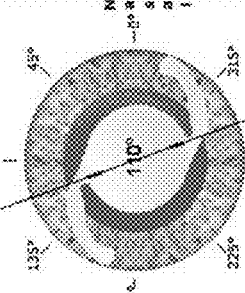
FIG. 4 shows exemplary external data including surgical parameters collected from an eye of a patient, according to an embodiment.
Figure 5:
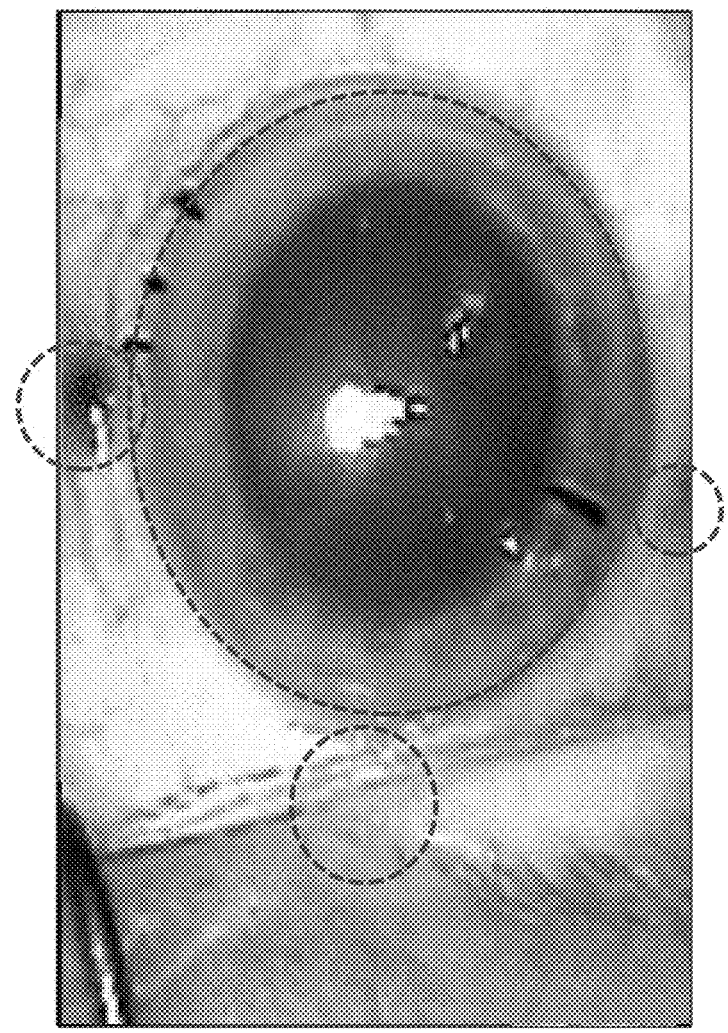
FIG. 5 illustrates exemplary external data including anatomical marks collected from an eye of a patient, according to an embodiment.

FIGS. 4 and 5 illustrate exemplary external data received from external data source 5, according to one embodiment.

The external data may include, for example, images acquired by other modalities, such as MRI, CT, Ultrasound, X-ray, etc. The external data may also include parameters of equipment utilized in the ongoing surgery, such as MICS parameters including vacuum pressure, ultrasound power, aspiration, bottle height; and battery status of eyewear device, etc. The external data may also include patient information, such as patient identification, patient history, heart rate, respiration rate, blood pressure, ECG, or other biological or physiological information. The external data may also include measurements taken prior to the surgery procedure and represent pre-operative anatomical characteristics of the patient or calculation details from the pre-operative measurements. For example, the external data may indicate myopia or hyperopia of the patient (in diopters), astigmatism of the patient, direction of axis of alignment of the patient's eye, locations of anatomical marks of the patient, contours of anatomical features of the patient, suggested locations for specification incisions, etc. The external data may also include, for example, the surgeon's personal information and identification, local time information, location information, etc.

At step 206, processing unit 4 generates composite digital image data based on the video data received from image source 3 and the external data received from external data source 5. The composite digital image data includes a representation of the external data superimposed or overlaid on the patient images in the video data. For example, processing unit 4 may generate the representation of the external data, such as an icon, a bar, a color-coded image, a text, etc., and modify individual frames of the video data to incorporate the representation of the external data.

At step 208, processing unit 4 transmits the composite digital image data to the display device for display to the surgeon. The display device receives the composite digital image data and display to the surgeon overlaid images from the composite digital image data. The overlaid images include a representation of the patient images included in the video data and a representation of the external data superimposed thereon. The representation of the external data may include an indication of a suggested incision or graphical and textual representations of surgical parameters overlaid on an image of an anatomical structure and registered to anatomical landmarks. In addition, the overlaid images may also include other information generated by processing unit 4 and superimposed on the patient images, such as graphical and textual prompts suggesting a specific surgical navigation or maneuver to the surgeon.

System 10 may assist the surgeon to carry out the surgical procedure using the overlaid images. For example, the overlaid images may display the surgical parameters superimposed on a representation of the patient images so that the surgeon may monitor the surgical parameters while viewing the patient images. In another embodiment, the overlaid images may display a suggested location for an incision on the patient image so that the surgeon may have a real-time reference for the incision. The overlaid images may also display a warning message alerting the surgeon to any abnormality during the surgical procedure, such as excessive ultrasound power or vacuum pressure. Thus, the surgeon may adjust the surgical equipment to bring the parameters within a desired range or to stop the surgery if necessary to protect the patient.

Steps 202-208 may be carried out by system 10 iteratively to provide real-time visual feedback to the surgeon. For example, as the surgeon carries out a surgical maneuver, system 10 may update the overlaid images to show the surgical maneuver to the surgeon through the display device so that the surgeon may reference the surgical maneuver to the overlaid representations of the external data. As another example, when the surgeon completes a surgical step, system 10 may automatically update the overlaid images to suggest a next step. Thus, the surgeon may carry out the surgical procedure without looking away from the display device or taking off eyewear device 7 and may still be able to monitor the parameters and receive information relevant to the surgery.

Figure 6:
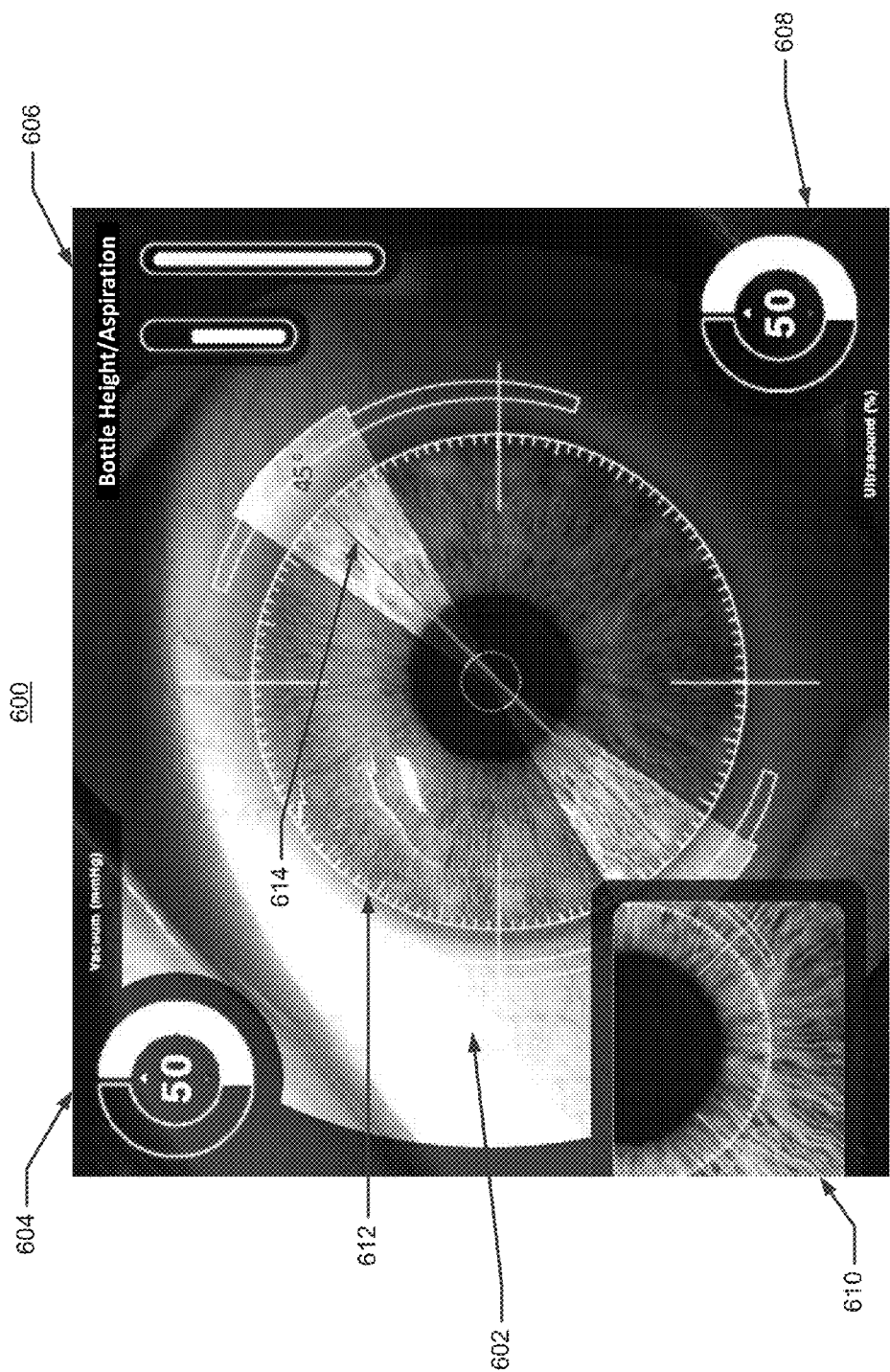
FIG. 6 illustrates an exemplary overlaid image displayed by the system of FIG. 1, according to an embodiment.

FIG. 6 illustrates an exemplary overlaid image 600 displayed by the display device to surgeon during the surgical procedure. Image 600 may include a central region 602 including a representation of the patient images from image source 3. Central region 602 may focus on or emphasize a region of interest within the field of view of image source 3. The region of interest may include an anatomical structure, such as an eye, upon which the surgical procedure is carried out. Image 600 may further include peripheral regions (604, 606, 608, and 610) having representations of the external data superimposed on the patient images. The representations of the external data may include, for example, icons, bars, charts, graphs, images, or text, which represent vacuum pressure (604), bottle height/aspiration (606), and ultrasound power (608), etc.

Image 600 may further include image features that are generated by processing unit 4 based on the external data. For example, image 600 may include a circular dial or protractor 612 corresponding to a patient's cornea or limbus. Circular dial 612 is superimposed on the patient images to indicate angular position with respect to the eye. The diameter of circular dial 612 may change when image 600 is zoomed in or out. Image 600 may also include a linear element 614 representing a suggested location of an axis of placement for a toric lens. Linear element 614 may provide the surgeon with a reference for placing and adjusting a toric lens during a cataract or astigmatism surgery. In another embodiment, image 600 may be formed by processing unit 4 to further include color codes or other image patterns distinguishing individual tissues or layers of tissue within the surgical field. For example, image 600 may include color-coded regions representing patient's cornea, limbus, iris, lens, pupil, etc. System 10 may determine the color-coded regions for the tissues based on pre-operative images, such as CT, MRI, ultrasound, OCT, etc., or intra-operative images or measurements collected during the surgical procedure.

The image features may further include arcs, "fans," or other geometrical shapes that are suitable for representing textual and graphical information in the patient images as well as the external data. These image features may be generated by processing unit 4 based on pre-operative measurements taken before the surgical procedure or based on feature detection and measurements performed intra-operatively during the surgical procedure using any of the external sources mentioned above with respect to FIG. 1. The image features may be magnified at different magnifications according to the representation of the patient images displayed by eyewear device 7. For example, when the representation of the patient images is zoomed in, the sizes of the image features may be increased accordingly. When the representation of the patient images is zoomed out, the sizes of the images may be decreased accordingly.

Figure 7:
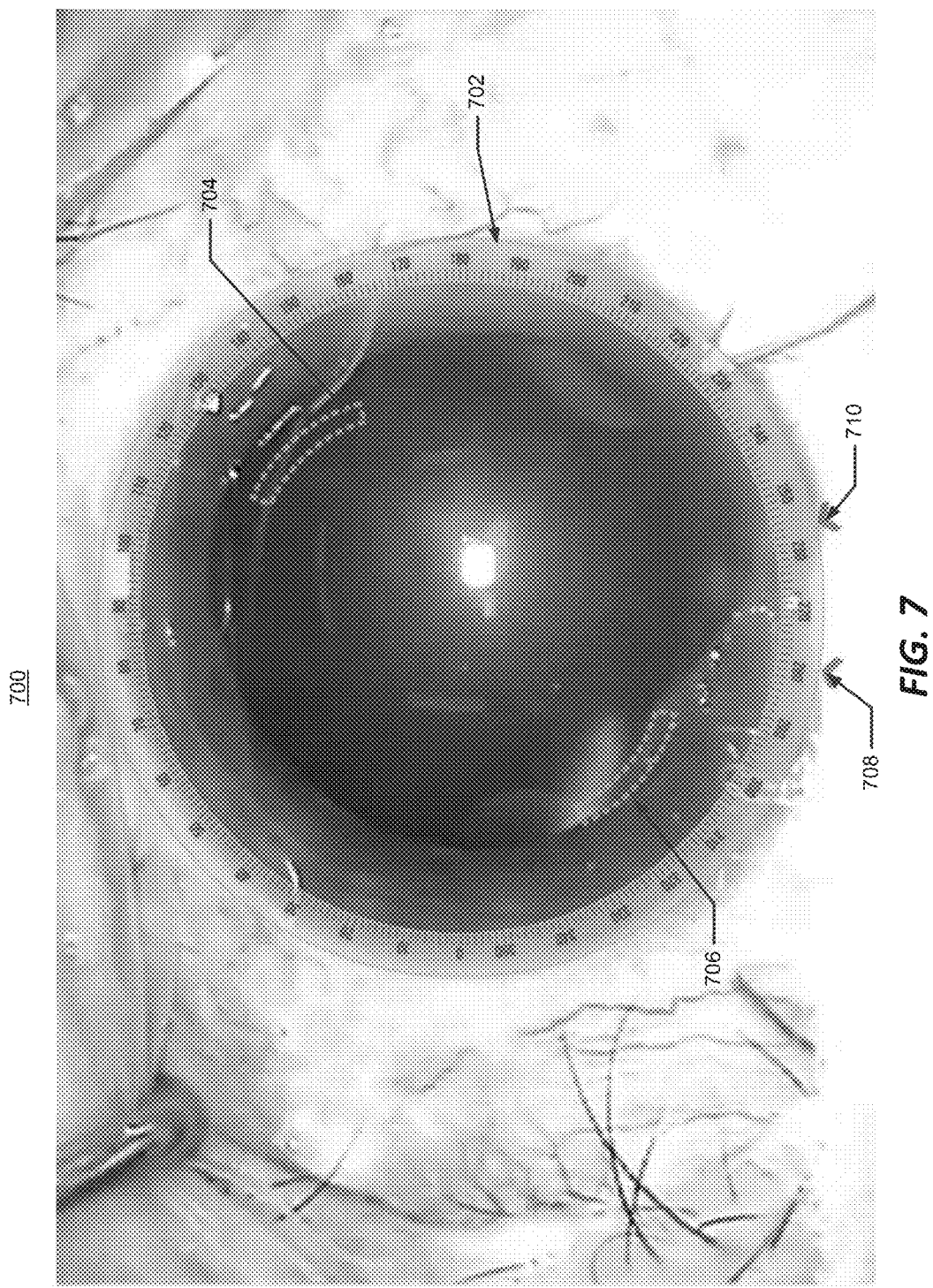
FIG. 7 illustrates an exemplary overlaid image displayed by the system of FIG. 1, according to another embodiment.

FIG. 7 illustrates another overlaid image 700 displayed by the display device, according to an embodiment. Similar to image 600, image 700 includes a protractor 702 further including numerical markings defining a circular coordinate system that allows the surgeon to visually determine angular locations of the anatomical features within the region of interest. In addition, image 700 includes representations of suggested incision points 704, 706, 708, and 710 to provide guidance and prompts for the surgeon to carry out the surgical procedure. For example, suggested incision points 704, 706, 708, and 710 may guide the surgeon to insert a surgical blade for cutting at a desired location/direction and allow the surgeon to instantaneously reference or check an actual cutting location against the suggested location. Image 700 may include different image features, such as colors or icons, to differentiate a primary incision point (e.g., 708) from a secondary incision point (e.g., 710), so as to assist the surgeon to direct a primary surgical instrument to the primary incision point and the secondary surgical instrument to the secondary incision point. These suggested incision points may be generated by processing unit 4 based on pre-operative measurements taken before the surgical procedure or based on intra-operative feature detection and measurements performed during the surgical procedure.

Figure 8:
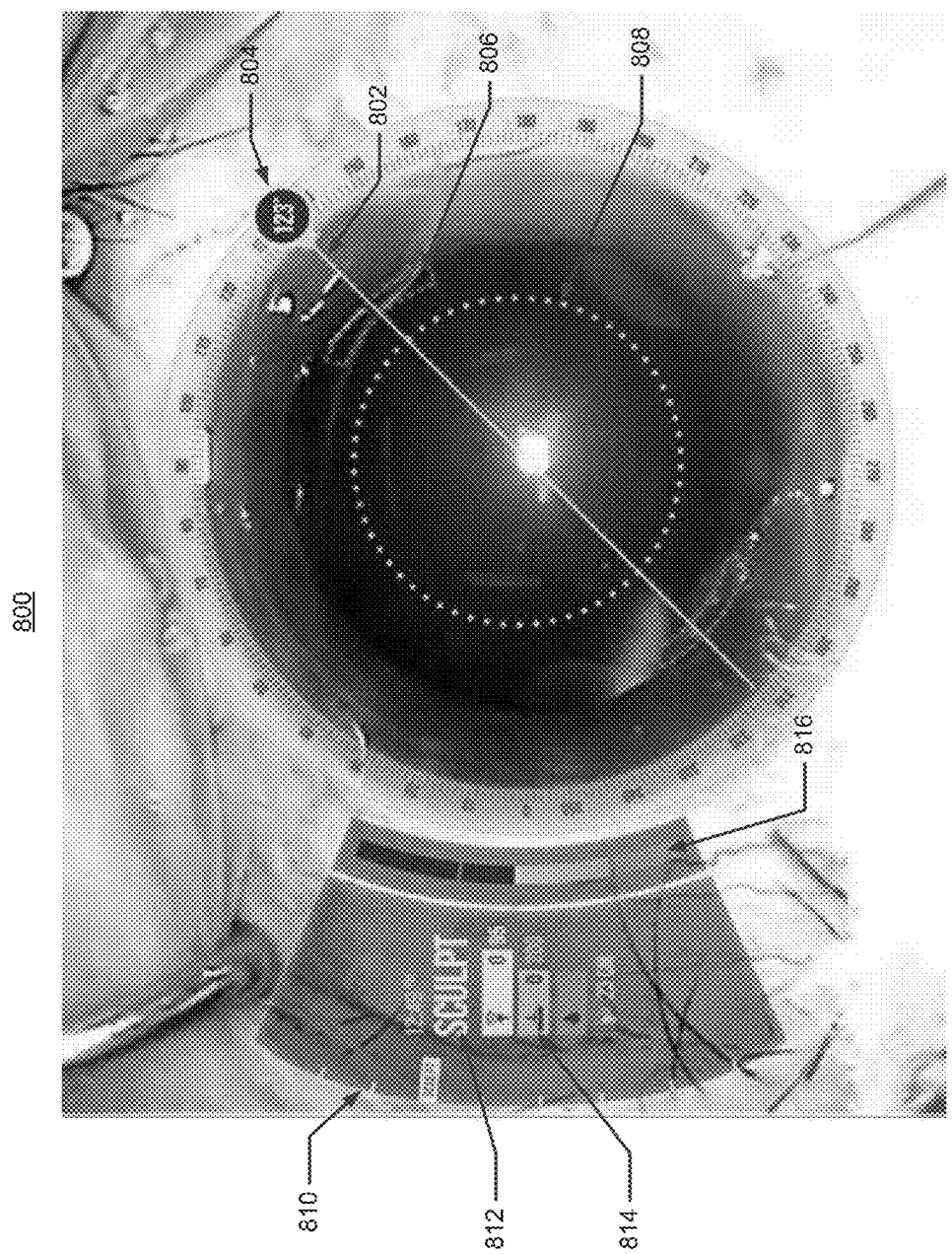
FIG. 8 illustrates an exemplary overlaid image displayed by the system of FIG. 1, according to another embodiment.

FIG. 8 illustrates an overlaid image 800 displayed by the display device, according to one embodiment. In addition to a linear element 802 indicating a steep axis (i.e., the axis of placement) for toric lens, image 800 may also include a text element 804 providing a numerical value of the angular location associated with the steep axis. This numerical value may further assist the surgeon to evaluate the astigmatism of the patient and correctly place the artificial lens during the surgical procedure. Moreover, overlaid images, based on pre-operative calculations and/or intra-operative measurements, when combined and registered with real-time images of the surgical field may result in more accurate surgical procedures and better patient outcomes.

Image 800 may further include a graphical element 806 representing suggested incision points for limbic incisions, registered with the real-time surgical field. Image 800 may align graphical element 806 with linear element 802 so as to guide the surgeon to make incisions along the steep axis. In one embodiment, processing unit 4 may determining locations for the graphical element 806 based on a distance to the center of pupil, the arc length of the incision, the depth of the incision. Processing unit 4 may also take into account other incisions to be made because additional incision may also introduce surgically induced astigmatism.

Image 800 may further include a circular element 808 indicating a suggested diameter for a capsulorhexis incision. Circular element 808 provides a visual prompt to assist the surgeon to create a proper opening in the cornea, thereby allowing the surgeon to correctly remove the cataract and insert the artificial lens during the surgery. Once again, use of pre-operative and intra-operative measurements to generate overlaid images registered with images of the real-time surgical field can allow the surgeon to dynamically modify planned steps in surgical procedures to attain more accurate surgical results and better patient outcomes.

Image 800 may further include a fan-shape virtual gauge 810 showing graphical and textual representations 812, 814, and 816 of real-time information during the operation. Virtual gauge 810 is disposed in close proximity to the anatomical structure under operation, such as the cornea, and includes a fan shape that generally corresponding to a curvature of the anatomical structure under operation. Thus, virtual gauge 810 provides a non-intrusive visualization panel during surgery that allows the surgeon to visualize surgical parameters and guidance along with the real-time images of the surgical field. In an embodiment, the fan shape of visual gauge 810 can be scaled to follow the curvature of the anatomical structure when the surgeon moves or zooms in and out the images displayed by the display device.

In an embodiment, virtual gauge 810 may include a text section 812 that displays textual representations of the external data, such as the local time and the current phase/stage/progress of the surgical procedure. The textual representations may vary according to the surgical step or phase of the procedure. Virtual gauge 810 may also include a chart section 814 that displays graphical and textual representations of the external data, such as ultrasound power, vacuum pressure, aspiration, bottle height, etc. These chart representations may include graphical elements, such as bar elements, which correspond to numerical values of the external data. For example, the lengths of the bar elements may vary in accordance with the numerical values of the external data. The graphical elements may be color coded to allow easy visualization and differentiation. The chart representations may further include textual elements corresponding to the numerical values of the external data. Virtual gauge 810 may further include a control section 816 that represents a status of a control input, such as a foot pedal, a switch, a button, a joystick, etc. Control section 816 may include characteristics, such as color or length, which vary with the status of the control input. The graphical elements coupled with the textual elements provided by gauge 810 allow the surgeon to quickly and promptly locate and monitor needed information during the surgical procedure without looking away from the surgical field or removing eyewear device 7.

Figure 9:
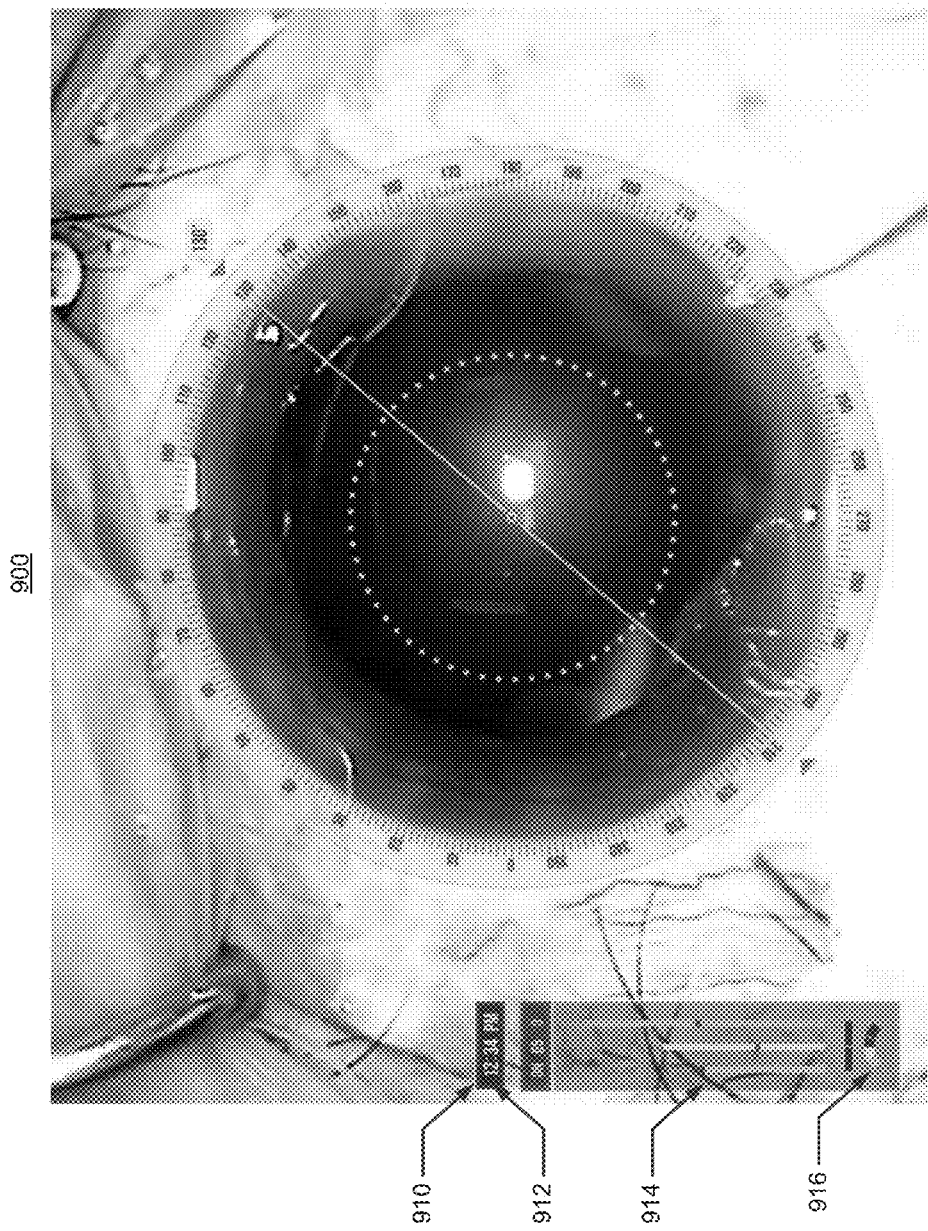
FIG. 9 illustrates an exemplary overlaid image displayed by the system of FIG. 1, according to another embodiment.

FIG. 9 illustrates an overlaid image 900 including a virtual gauge 910. Virtual gauge 910 may have a rectangular shape disposed at a corner of the region of interest displayed by the display device. Virtual gauge 910 may include a text section 912 showing textual information, such as the local time and the phase of the surgical procedure. Virtual gauge 910 may also include a chart section 914 showing graphical representations of the external data, such as the ultrasound power, the vacuum pressure, the aspiration, etc. Virtual gauge 910 may further include a control section showing the status of the control input as discussed above.

Figure 10:
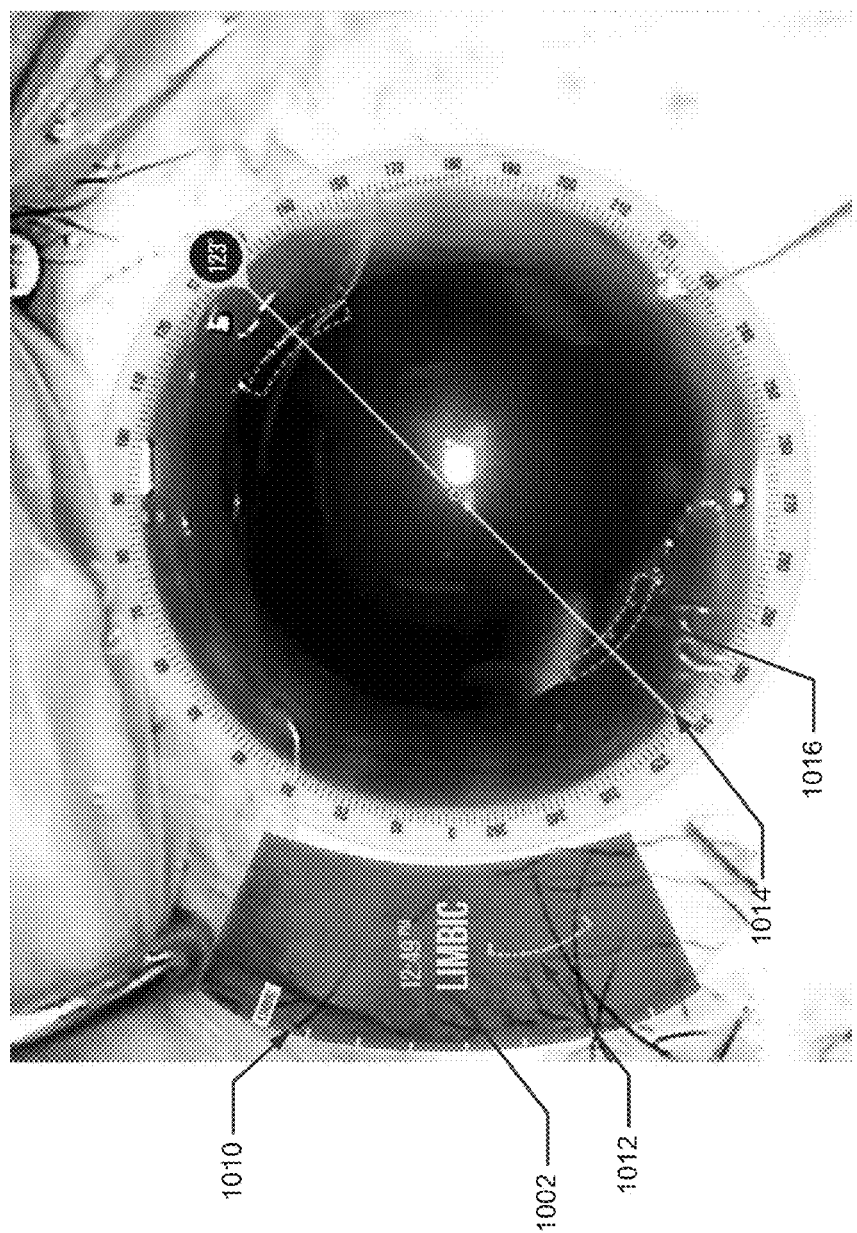
FIG. 10 illustrates an exemplary overlaid image displayed by the system of FIG. 1, according to another embodiment.
Figure 11:
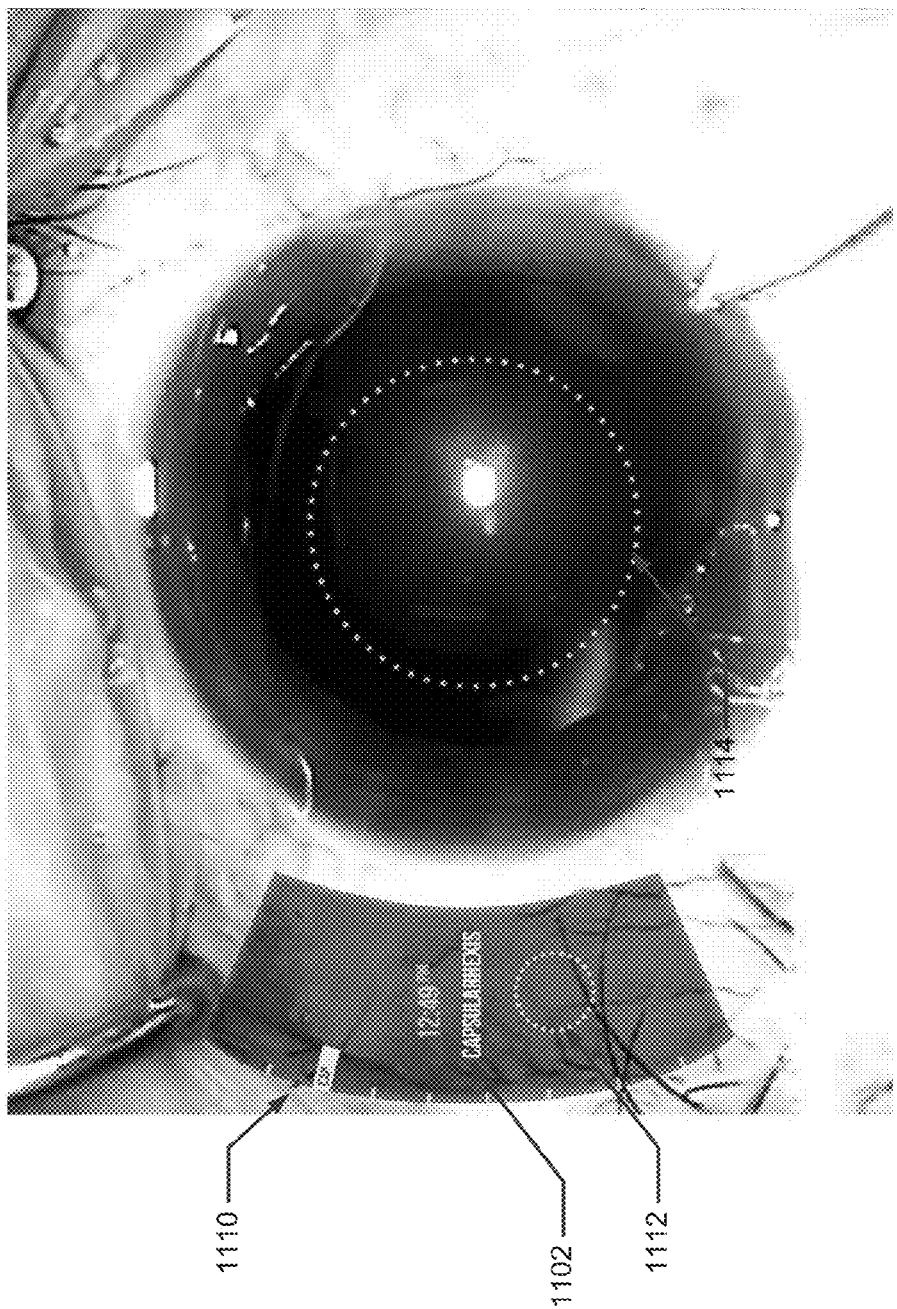
FIG. 11 illustrates an exemplary overlaid image displayed by the system of FIG. 1, according to another embodiment.
Figure 12:
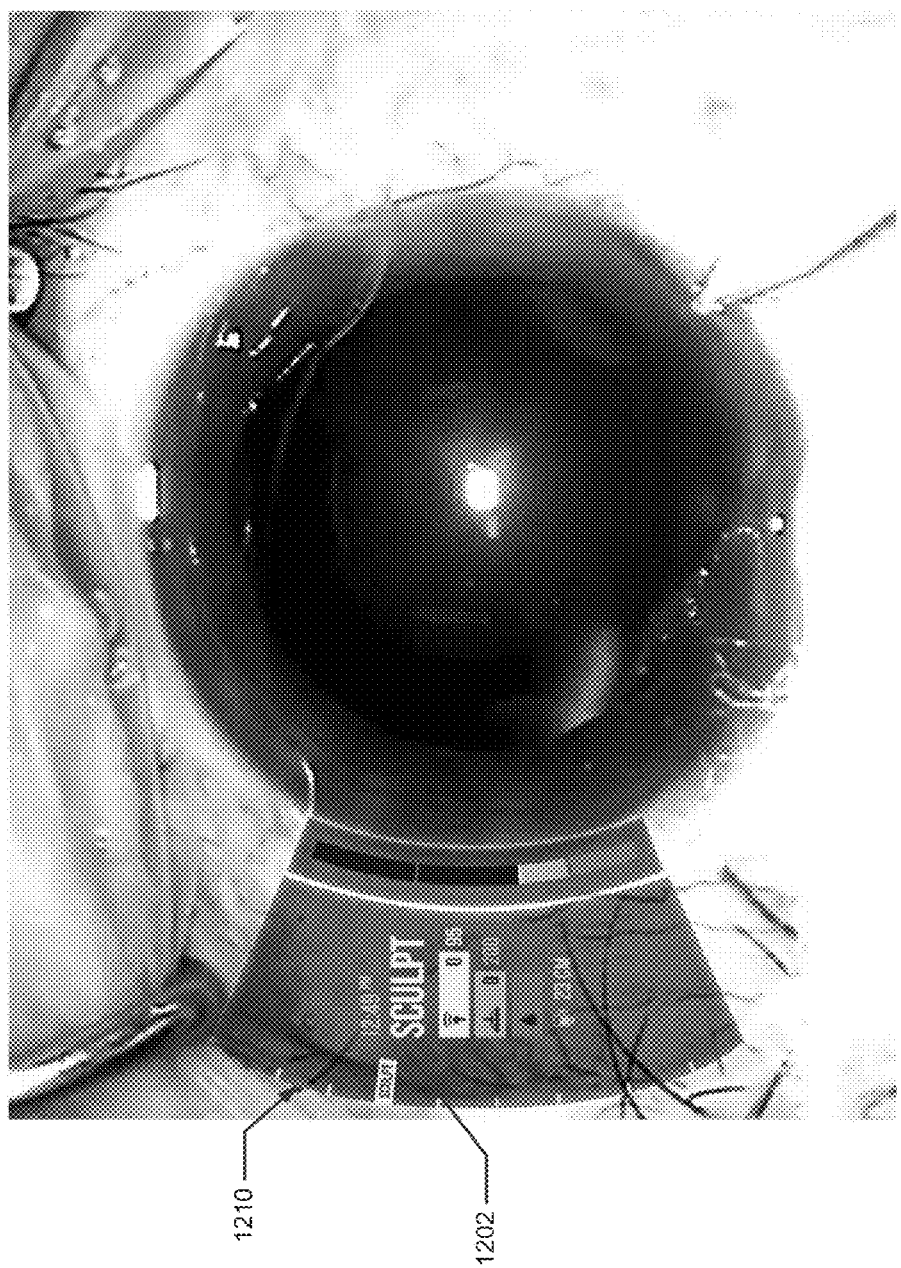
FIG. 12 illustrates an exemplary overlaid image displayed by the system of FIG. 1, according to another embodiment.

FIGS. 10-12 illustrate an embodiment of a cataract surgery process with the assistance of system 10. In FIG. 10, the display device displays a representation of the patient image with a virtual gauge 1010 overlaid thereon showing a textual message "LIMBIC" 1002 and an arc icon 1012, prompting the surgeon to perform a limbic incision on the patient's eye. The display device may further display a protractor image showing angular locations of the cornea and the limbus area of the eye. To assist the surgeon in carrying out the incision, the display device may further display a linear element 1014 indicating the steep axis and graphical marks 1016 suggesting incision points. The surgeon may then position a microscalpel to follow the graphical marks in making the incision.

In FIG. 11, after the limbic incision is performed, the display device may display a textual message "CAPSULORHEXIS" 1102 with a circular icon 1112 in a virtual gauge 1110, prompting the surgeon to perform a capsulorhexis procedure. To assist the surgeon in carrying out the capsulorhexis incision, the display device may further display a circular mark 1114 indicating the suggested incision points for the capsulorhexis procedure. The surgeon may then follow the circular mark in making incisions on the capsule of the patient's lens.

In FIG. 12, after the capsulorhexis procedure is carried out, the display device may display a textual message "SCULPT" 1202 in a virtual gauge 1210 with graphical representations of the external data as shown in FIG. 8, prompting the surgeon to carry out a sculpt procedure.

During the sculpt procedure, the surgeon may use an ultrasound instrument or other equipment to cut or break apart the patient's natural lens, according to techniques known in the art. The graphical representations in the virtual gauge allow the surgeon to monitor the parameters of the equipment in real time while carrying out the cutting. The virtual gauge also allows the surgeon to adjust the equipment as desired according to the real-time visual feedback provided by the virtual gauge.

Although not shown, one skilled in the art will also appreciate that system 10 may be adopted to assist the surgeon to perform various other procedures known in the art. For example, after the sculpt procedure, eyewear device 7 may display any one or more of the following messages: a text message "QUADRANT REMOVAL" prompting the surgeon to remove large chunks of the cataract using the vacuum instrument; a text message "EPINUCLEUS" prompting the surgeon to remove remaining epinucleus layer of the lens; a text message "IRRIGATION & ASPIRATION" prompting the surgeon to clean and remove any leftover material more thoroughly using smaller instruments with lower vacuum pressure; a text message "POLISH" prompting the surgeon to posh the lens capsule; a text message "INSERT LENS" prompting the surgeon to insert an artificial lens to replace the removed lens; or a text message "VISCOUS ELASTIC REMOVAL" prompting the surgeon to aspirate out viscous fluid. These messages may be coupled with proper graphical icons and graphical representations of the external data similar to those described above to assist the surgeon to make proper decision and surgical maneuver.

Figure 13:
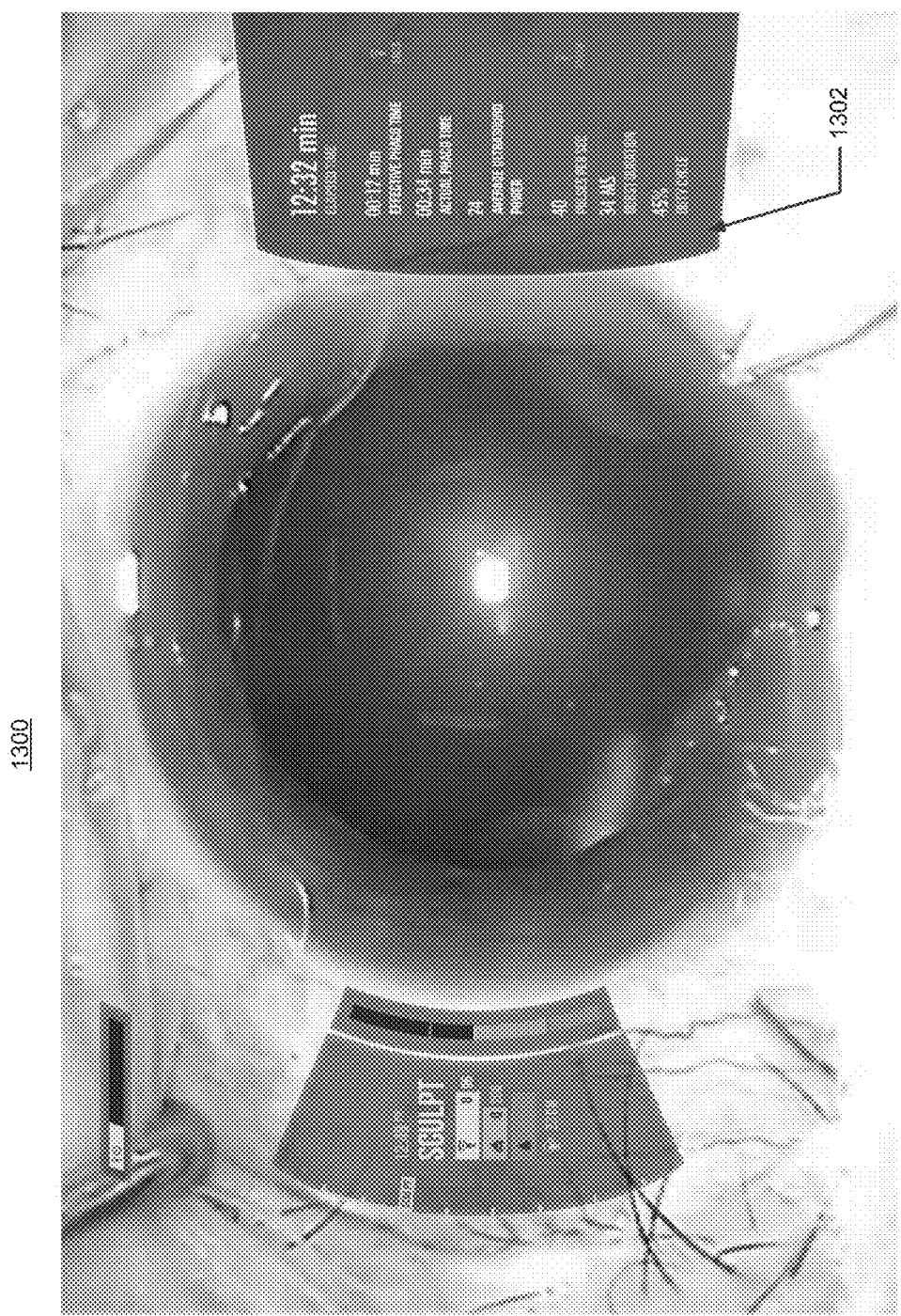
FIG. 13 illustrates an exemplary overlaid image displayed by the system of FIG. 1, according to another embodiment.

FIG. 13 illustrates an overlaid image 1300 including an additional panel 1302 displayed to the surgeon by system 10 through the display device. Panel 1302 may also be overlaid on the representation of the patient images in a portion of the region of interest and in proximity to the anatomical structure under operation. Panel 1302 may display other portions of the external data that include statistics relevant to the surgical procedure, such as timing statistics (e.g., elapsed time, effective time, etc.) or equipment statistics (e.g., average ultrasound power, pulses per second, burst duration, duty cycle, etc.). These statistics allow the surgeon to further monitor the surgical equipment and ensure the procedure is carried out properly.

Figure 14:
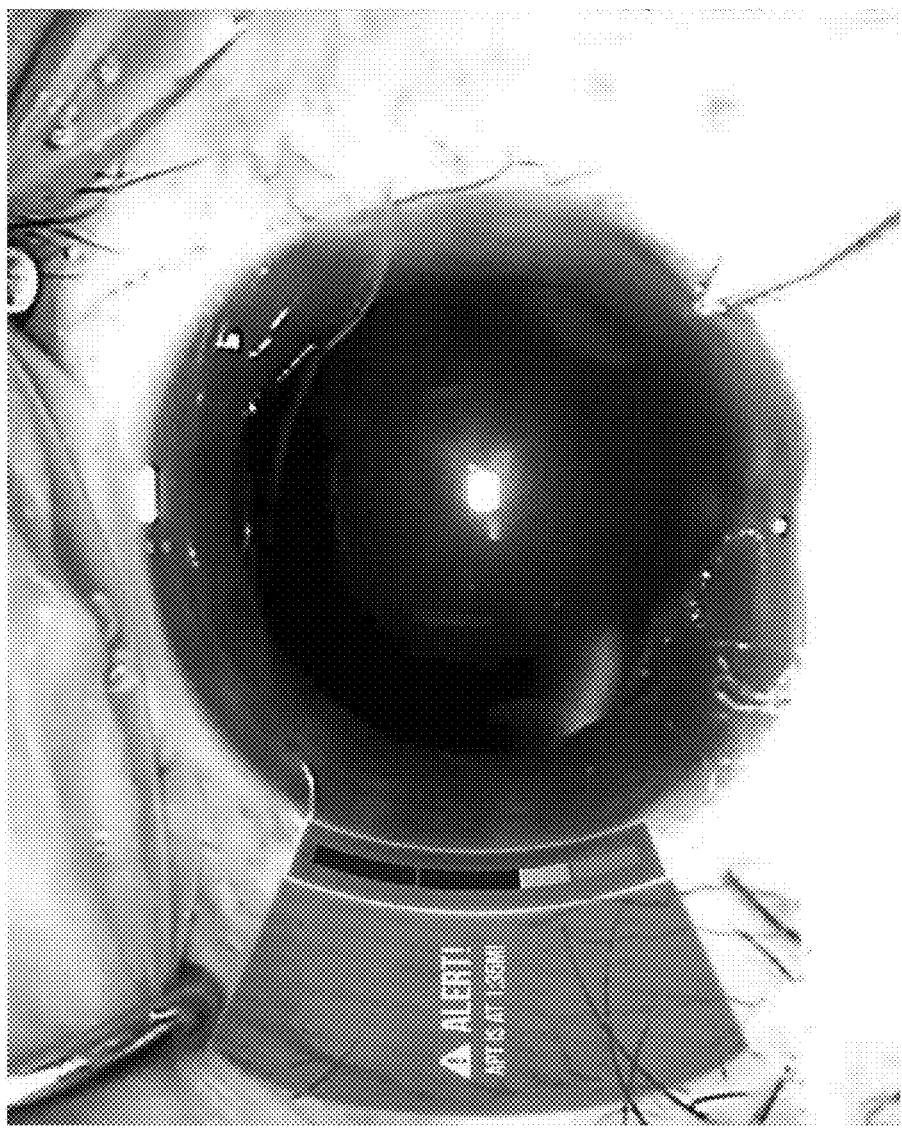
FIG. 14 illustrates an exemplary overlaid image displayed by the system of FIG. 1, according to another embodiment.

FIG. 14 illustrates a warning message, which may be generated by system 10 and displayed by the display device, when system 10 detects an alert condition during the procedure, such as an approaching high limit of ultrasound energy applied in the procedure. The warning message may include a graphical icon with a prominent feature, such as the color red, and be displayed at a prominent location, alerting the surgeon to an abnormality during the surgery. In one embodiment as shown in FIG. 14, the warning message replaces the graphical and textual representations of the external data and occupies a substantial portion of the virtual gauge. The warning message may further include text messages providing detailed information about the abnormality to allow the surgeon to pinpoint the source that causes the abnormality. For example, the warning message may alert the surgeon to excessive/insufficient ultrasound power, excessive/insufficient vacuum pressure, excessive/insufficient aspiration, excessive/insufficient bottle height, etc. In response to the warning message, the surgeon may adjust the surgical instruments to bring the parameters into a desired range. For example, in a phaco-emulsification procedure, removal of the cataract may cause materials at the rear half of the lens capsule to move closer to the tip of the instrument. System 10 allows the surgeon to monitor the power and pressure of the instruments in real time to prevent the lens capsule from breaking and avoid complications that may cause vitreous fluid in the lens to come forward. System 10 also allows the surgeon to monitor the ultrasound power and energy and to prevent excessive ultrasound power that may overheat the patient's organ or tissue, thereby preventing complications. System 10 also allows the surgeon to adjust the surgical parameters, such as ultrasound power, vacuum pressure, bottle height, etc., during the procedure to meet specific needs and requirements.

In an embodiment, system 10 may adjust the elements of the overlaid images, such as the virtual gauge, the additional panel, etc., according to the needs of the surgeon. For example, system 10 may relocate the virtual gauge or the additional panel to other areas of the overlaid images. System 10 may show or hide the virtual gauge or the additional panel as desired by the surgeon. System 10 may receive instructions from the surgeon to customize the information and message displayed in the virtual gauge and the additional panel.

Figure 15:
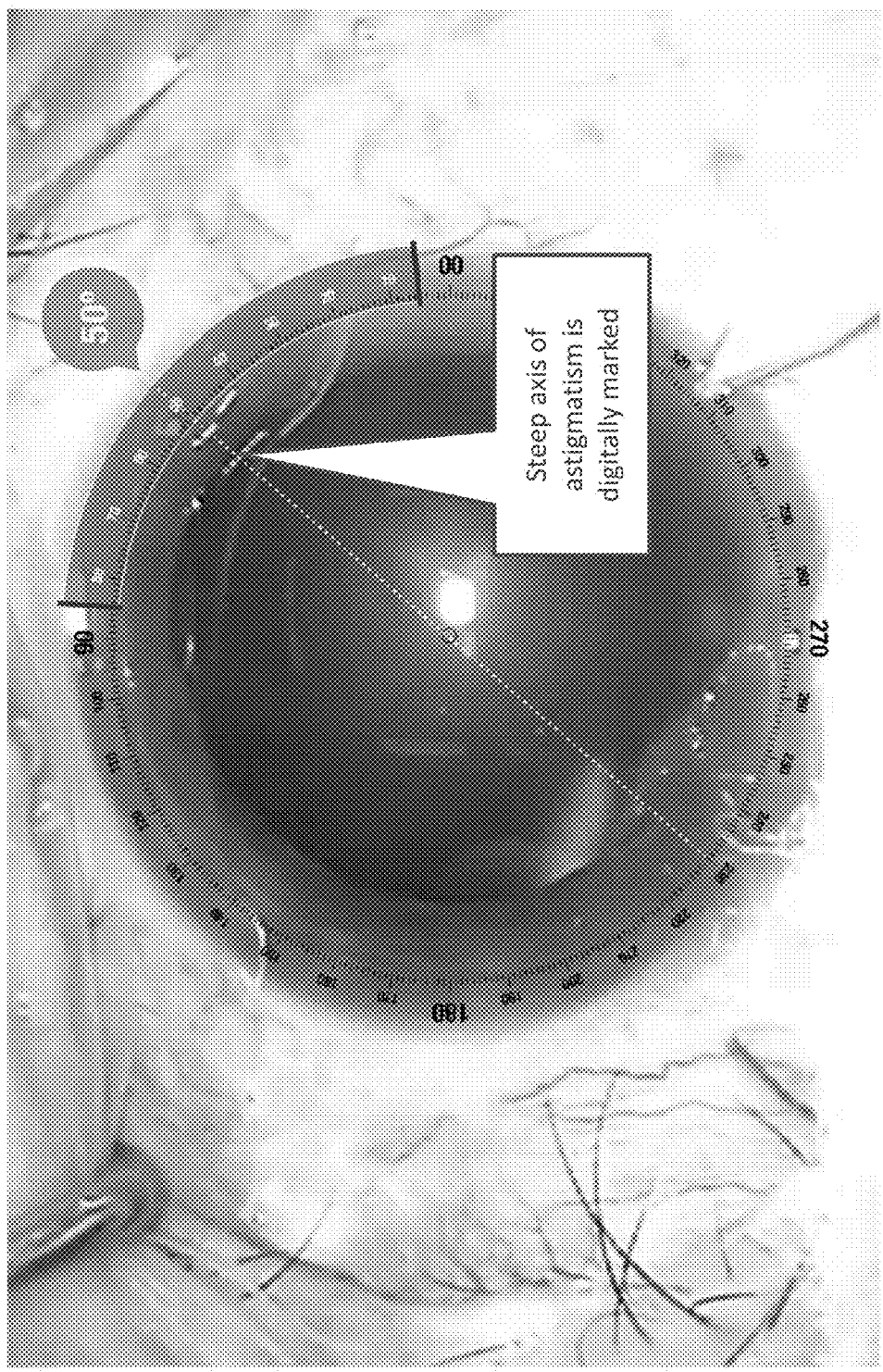
FIG. 15 illustrates an exemplary overlaid image displayed by the system of FIG. 1, according to another embodiment.
Figure 16:
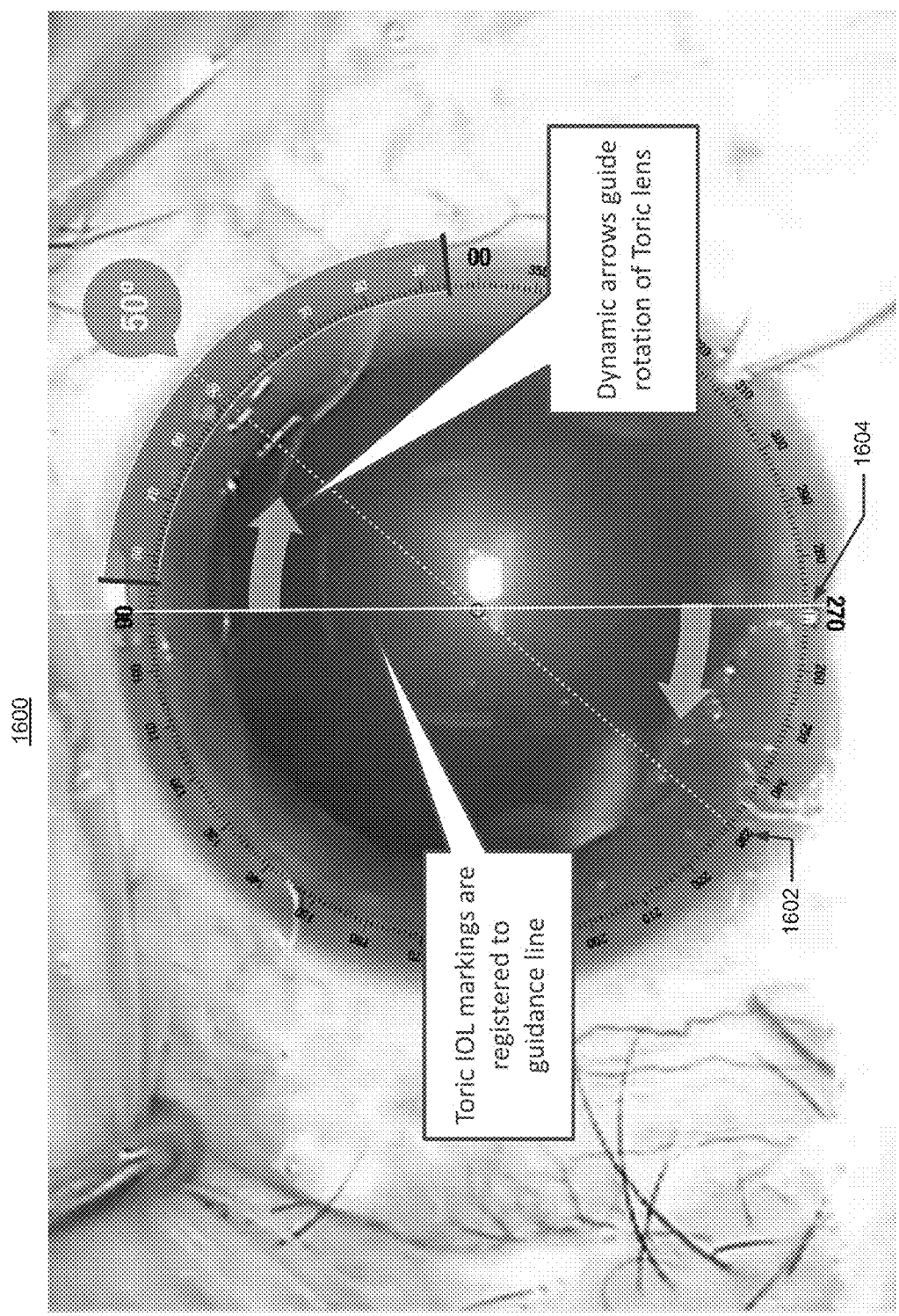
FIG. 16 illustrates an exemplary overlaid image displayed by the system of FIG. 1, according to another embodiment.
Figure 17:
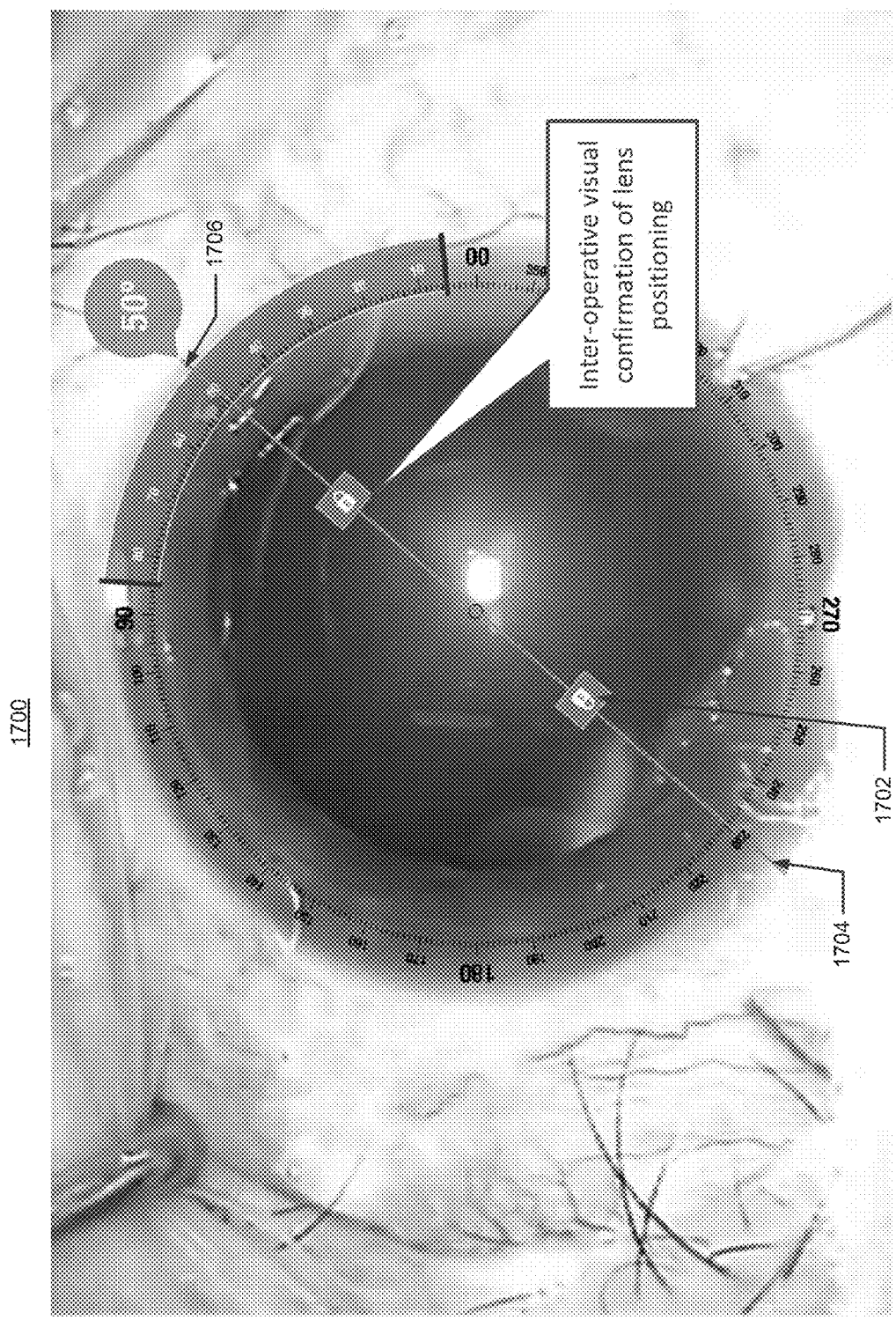
FIG. 17 illustrates an exemplary overlaid image displayed by the system of FIG. 1, according to another embodiment.

FIGS. 15-17 illustrates an exemplary process of lens insertion during the cataract or astigmatism surgery assisted by system 10. In FIG. 15, system 10 displays a steep axis of astigmatism for the patient's eye based on external data. The external data may include pre-operative measurements such as those shown in FIG. 4 that allows processing unit 4 to determine the proper location for the axis. Alternatively, system 10 may determine the axis based on intra-operative measurements obtained during the surgery. As shown in FIG. 15, system 10 may digitally mark the location of the axis using a linear element with text showing a numeral value of the degree of the axis with respect to the circular coordinates defined by the protractor. System 10 may display the location of the axis after all of the cataract materials are removed from the patient's eye and when the artificial lens is ready to be inserted.

In FIG. 16, when the surgeon inserts an artificial lens, such as a toric intraocular lens (IOL), into the patient's eye, system 10 determines a position 1604 of the lens in the patient's eye and compares the position of the lens to a guidance line 1602. System 10 may display the guidance line to the surgeon in the overlaid image with respect to the mark indicating the location of the steep axis, so as to provide visual feedback to the surgeon about the spatial relationship between the lens and the steep axis. System 10 may also display a directional indicator, such as a dynamic arrow, prompting a rotation of the lens by the surgeon. The directional indicator may point from the guidance line toward the steep axis, prompting the surgeon to rotate the lens in a suggested direction. The directional indicator may be dynamically adjusted to follow the guidance line as the surgeon rotates the lens. In a further embodiment, system 10 may periodically recalculate the guidance line according to the rotation of the lens and update the location of the guidance line accordingly. When the guidance line is sufficiently close to the steep axis, such as within 5 degrees, system 10 may generate visual feedback, such as a textual message, a graphical message, or a color change of the guidance line, through eyewear device 7 alerting the surgeon that the lens is approaching its desired position.

In FIG. 17, system 10 may determine a coincidence between the guidance line and the steep axis and display an intra-operative visual confirmation indicating to the surgeon that the lens has been properly positioned in the patient's eye. For example, the system 10 may display a lock icon 1702 on the coincident steep axis 1704 and guidance line 1706 indicating that the proper position of the lens. System 10 may also change the color of guidance line 1706 to a more prominent color indicating the proper positioning of the lens.

Figure 18B:
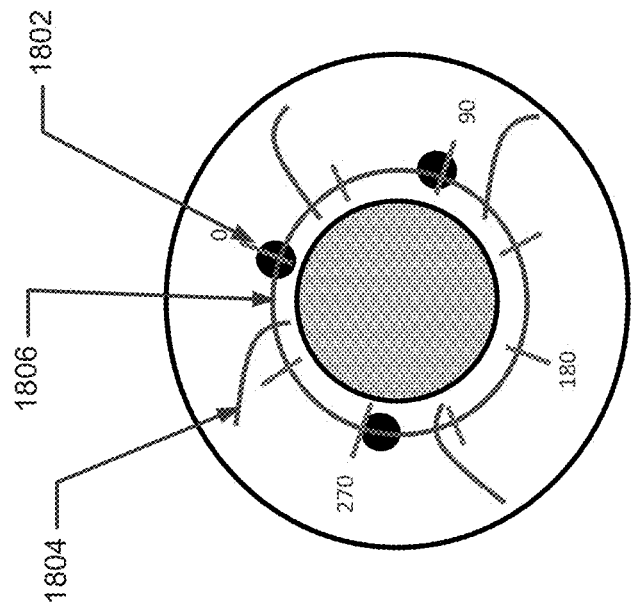
FIGS. 18A and 18B illustrate a feature identification process for registering different images of a patient, according to an embodiment.
Figure 18A:
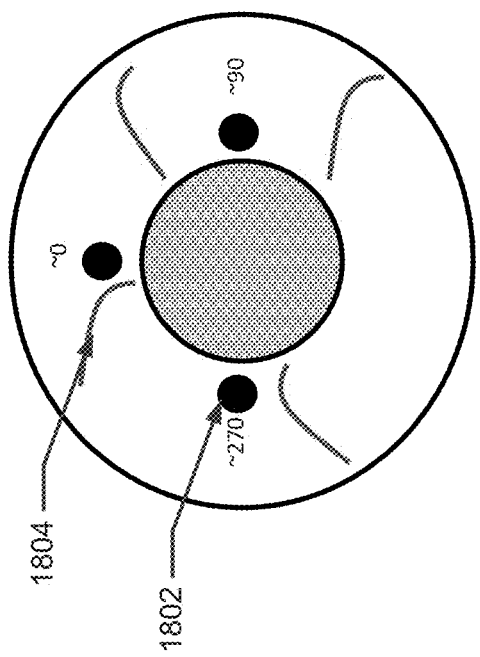

FIGS. 18A and 18B illustrate a feature identification process implemented by system 10, according to one embodiment. System 10 may use the feature identification to identify anatomical features or structures, such as the cornea, the iris, the limbus, etc., during a surgical procedure. As shown in FIG. 18A, system 10 may first determine one or more identifying features on the patient's tissue or organ based on known technique such as computer-aided feature extraction and identification. The marks may be artificial marks 1802 placed on the patient by the surgeon or other medical staff or specific anatomical features 1804, such as blood vessels, which are visually prominent and easy to identify. System 10 may associate the marks with coordinate indications, such as 0 degree, 90 degrees, or 270 degrees, indicating the relative spatial relationships of the marks. System 10 may identify the marks pre-operatively (before a surgical procedure) based on input received from the surgeon or medical staff. Alternatively, system 10 may identify the marks intra-operatively (during the surgical procedure) based on the external data received from external data source 5 or based on real-time video data received from image source 3 during the operation.

In FIG. 18B, system 10 identifies a desired anatomical structure based on the marks during the surgical procedure. In an embodiment, system 10 identifies an orientation of a cornea or a limbus of the patient's eye, based on the marks, and defines a circular coordinate system based on the identified anatomical feature and the coordinate indications associated with the marks. System 10 may display a circular protractor 1806 similar to that of FIG. 7 representing the circular coordinate system.

FIGS. 19A and 19B illustrate a feature tracking process implemented by system 10, according to an embodiment. In FIG. 19A, system 10 first identifies one or more marks, which may be artificial marks 1902 or anatomical marks 1904, similar to those marks shown in FIG. 18A. System 10 may then define a coordinate system 1906 based on the identified marks. System 1906 may be any coordinate system known in the art, such as a Cartesian coordinate system or a circular system. System 10 may determine and recognize the marks and the coordinate system pre-operatively or intra-operatively using known techniques based on the external data or real-time video data collected from image source 3 during the surgery. After the marks are identified and determined, system 10 may register real-time images of the surgical field to the identified marks by "locking" the identified marks to corresponding anatomical features within the real-time images. System 10 may then track movements of the anatomical features based on the marks during a surgical procedure.

In FIG. 19B, when the patient or the surgeon moves during the surgery, the perspective of patient images obtained later in the surgical procedure may be different from those obtained pre-operatively or early in the surgical procedure. As a result, the locations and/or perspectives of the anatomical features within the patient images as viewed by the surgeon through the display device also change. System 10 may then register the anatomical features in the later patient images to those in the earlier patient images based on the marks and the coordinate system. System 10 may then track the anatomical features during the surgical procedure even when their locations/orientations change within the patient images.

FIGS. 20A and 20B illustrates a process 2000 for adjusting a region of interest of the overlaid images displayed by the display device, according to an embodiment. In this embodiment, image source 3, such as cameras 3a and 3b, has a high-resolution image sensor 2002 that generates a field of view (FOV) 2006. Field of view 2006 may include an area or a portion of the patient, which the surgeon intends to examine or perform a surgical procedure on. Sensor 2002 may allow image source 3 to generate high-resolution patient images corresponding to a relatively large area of the patient.

The display device may display a portion of the high-resolution patient images corresponding to a region of interest (ROI) 2004, which is smaller than field of view 2006. As a result, the surgeon may view only the portion of the high-resolution patient images within region of interest 2004. The surgeon may adjust region of interest 2004 within field of view 2006 so as to view a desired region through the display device. For example, a motion sensor 14 (shown in FIG. 1), such as an inertia sensor, a laser sensor, an RF sensor, or other sensors known in the art may be employed or embedded in eyewear device 7 or attached to the surgeon's head. Motion sensor 14 may detect a motion of the surgeon and generate a motion signal to processing unit 4. Processing unit 4 may then determine, based on the motion signal, an updated location of region of interest 2004 within field of view 2006 and generate the overlaid images corresponding to the updated location of region of interest 2004. As a result, the overlaid images may show different regions of the patient images according to the motions of the surgeon.

In a further embodiment, motion sensor 14 may detect a head motion of the surgeon when the surgeon moves his/her head. The motion signal may indicate the head motion of the surgeon, such as turning left, right, up, or down. Upon receiving the motion signal from the motion sensor, processing unit 4 may determine a rotational angle, a rotational speed, and/or a rotational direction of the surgeon's head based on the motion signal. Processing unit 4 may further update the location of region of interest 2004 according to the rotational angle, the rotational speed, and/or the rotational direction. Processing unit 4 may then update the overlaid images to show the patient images within the updated region of interest. As a result, process 2000 provides an immersive virtual reality rendering of the patient images and allows the surgeon to view any desired region of the field of view by, for example, turning his/her head towards that region. According to an embedment, region of interest 2004 of the display device may have a magnification greater than that of the field of view 2006 of image source 3. The magnification may be controlled by the surgeon. Thus, the display device may allow the surgeon to view a more magnified representation of the surgical field when desired. Because image source 3 is able to produce high-resolution image data, the magnified representation generated by the display device would not cause significant blurring of the overlaid images.

Figure 21:
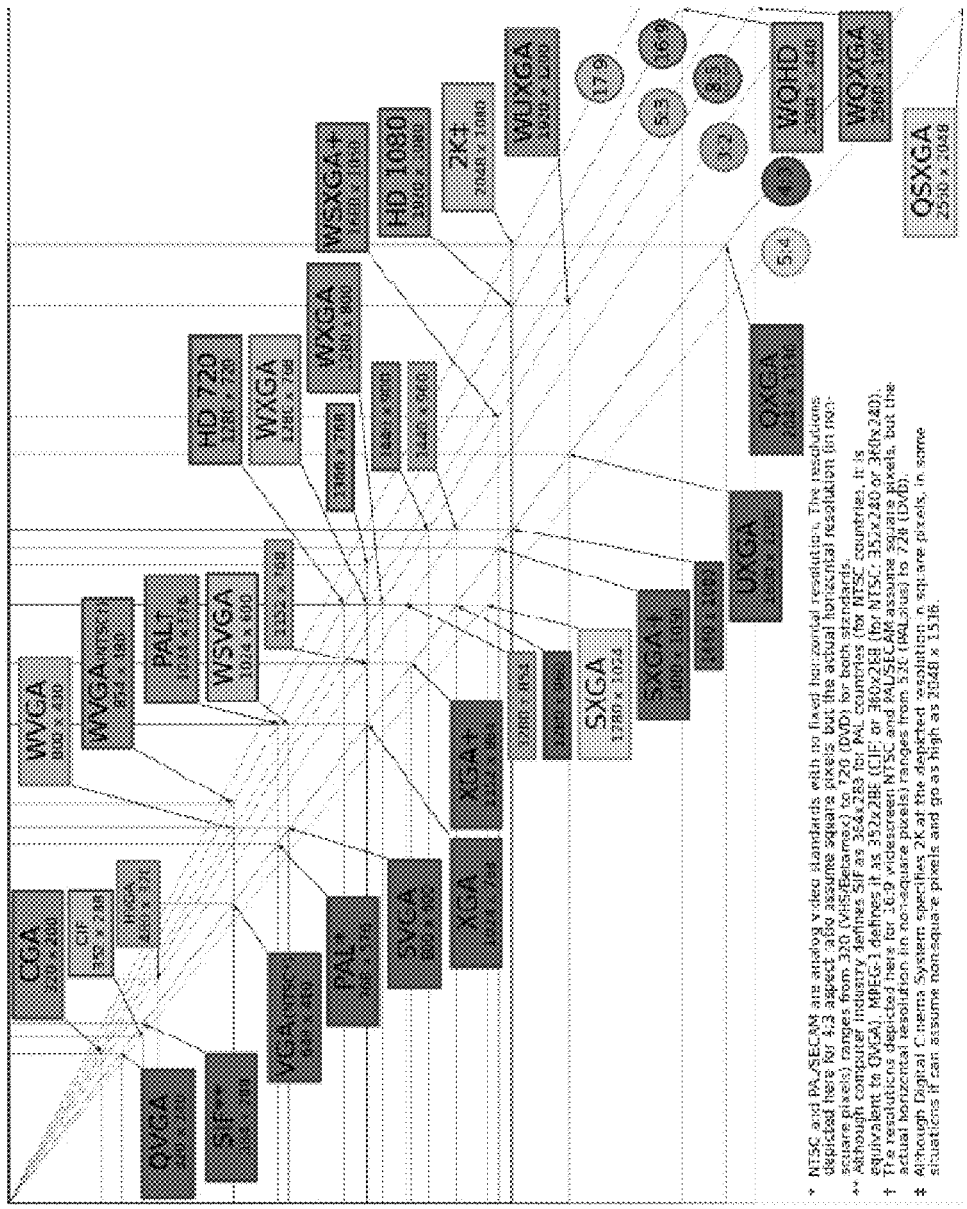
FIG. 21 illustrates exemplary video standards and formats supported by system of FIG. 1, according to some embodiments.

FIGS. 21-28 illustrate various hardware and software implementations of system 10, according to some embodiments. FIG. 21 illustrates the video standards and formats that may be supported by processing unit 4 and the display device. One skilled in the art will appreciate that the video standards and formats illustrated in FIG. 21 are for illustrative purposes only and that system 10 may support other video standards and formats not listed therein.

Figure 22:
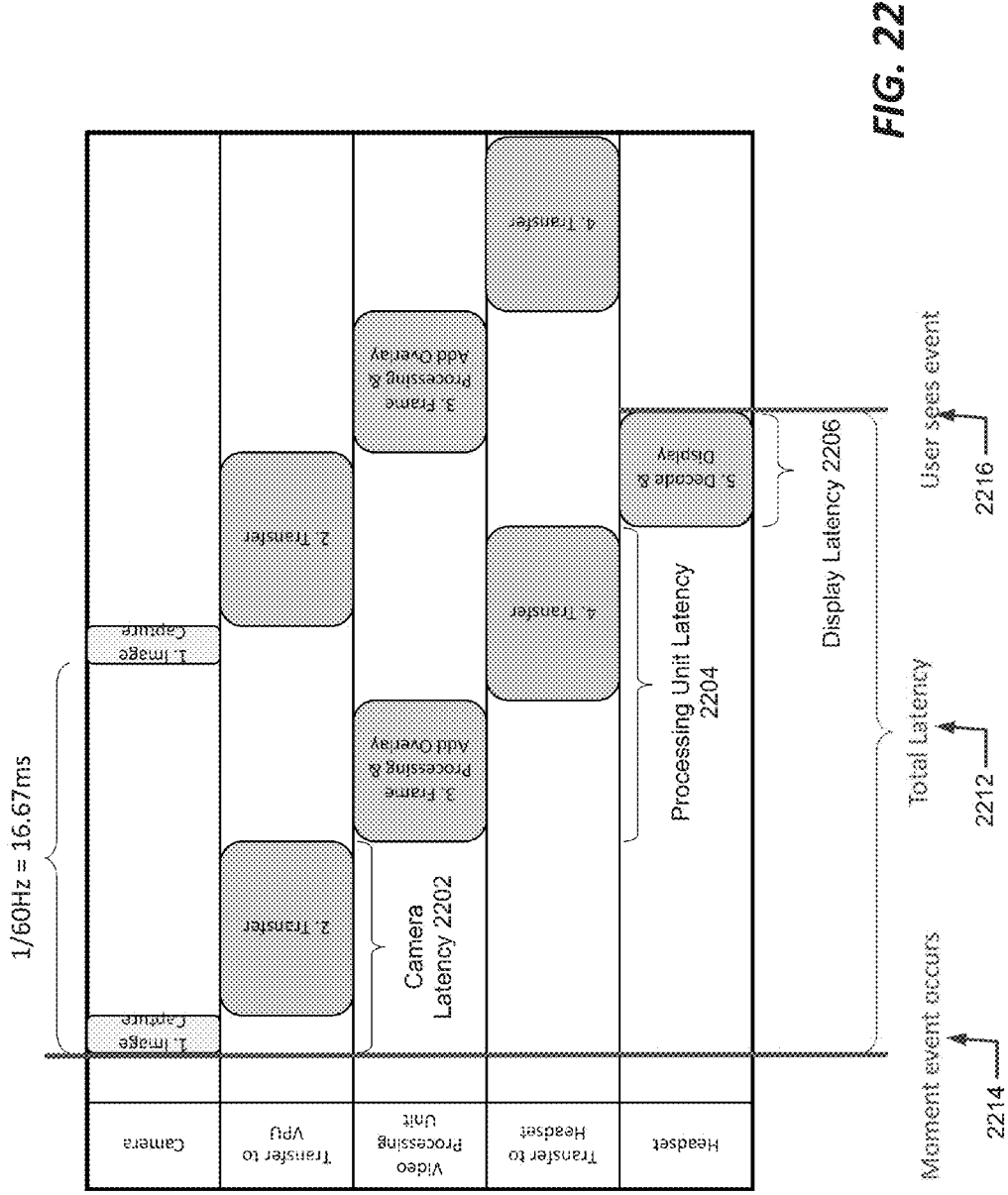
FIG. 22 illustrates latency which may be exhibited by system of FIG. 1, according to an embodiment.

FIG. 22 illustrates latency that may be exhibited by system 10 from image source 3 to the display device, according to one embodiment. System 10 may introduce a total latency 2012 between a first time 2214 when an event occurs at the surgical field and a second time 2216 when a representation of the event is displayed to the surgeon by the display device. Total latency 2012 may include a plurality of component latencies caused by components of system 10, including, for example, a camera latency 2202, a processing unit latency 2204, and a display latency 2206. Camera latency 2202 may be caused by triggering, exposure, and readout by image source 3 during acquisition of the video data. Processing unit latency 2204 may be caused by execution of the instructions for frame processing and overlaying and the data transfer to the display device. Display latency 2206 may be caused by decoding and rendering by the display device.

In an embodiment, system 10 has a maximum total latency of 16.67 ms (a 60 Hz frame rate equivalent). In particular, camera latency 2202 may be 8 ms or less at 60 frames per second minimum and a resolution of 720p or better. Processing unit latency 2204 may be less than 7 ms including time for data transfer and encoding. Display latency 2206 may be less than 1 ms.

FIG. 23 illustrates a transfer rate requirement for data transmission between image source 3 and processing unit 4 and between processing unit 4 and the display device. In general, higher resolutions and greater color depth require greater transfer rates in order to achieve a 60 Hz frame rate at the display device. System 10 may be configured to provide both a 720p resolution, a 1080p resolution, or other resolutions with a desired frame rate.

In an embodiment, processing unit 4 is configured to process inputs from image source 3 and external data source 5, create overlaid images with the external data superimposed on the patient images, and output the overlaid images to the display device to provide a stereoscopic rendering of the surgical field and the overlaid external data. Processing unit 4 may also convert the video data generated by image source 3 between different standards or formats.

In one embodiment, processing unit 4 has the following features:
 TCP/IP bus—interfaces with external data source 5, such as the Stellaris system;
 24 Digital inputs/outputs—provides user input buttons, diagnostic LED output, etc.;
 2 High-speed camera input buses—capable at minimum of supporting 720p (1280×720), 24 bit color, at 60 Hz frame rate (1.33 Gbit/sec);
  Specific resolution, color depth, and frame rate may be adjusted after surgeon feedback events;
  Sample formats and their data rates may include:
   HD-SDI/3G-SDI—2.97 Gbit/sec;
   CameraLink (Base)—2.04 Gbit/sec;
   CameraLink (Med)—4.08 Gbit/sec;
   CameraLink (Full)—5.44 Gbit/sec;
   GigE—1 Gbit/sec;
   10 GigE—10 Gbit/sec;
   Firewire 1600—1.6 Gbit/sec;
   Firewire 3200—3.2 Gbit/sec;
   USB 3.0—5 Gbit/sec;
 1 High speed expansion bus—for system expansion to provide speed processing and transmission;
  Sample formats and their transfer rates may include:
   USB 3.0—5.0 Gbit/sec;
   SATA III—6.0 Gbit/sec;
   PCIe 2.0 ×4—16 Gbit/sec;
   PCIe 2.0 ×8—32 Gbit/sec;
   PCIe 2.0 ×16—64 Gbit/sec;
 2 High speed video outputs—for stereoscopic display;
  Throughput should at minimum match camera input throughput;
  Sample formats may include:
   VGA;
   HDMI/DVI;
   Displayport—1.30, 2.16, 4.32 Gbit/sec PER LANE (@ 162, 270, 540 MHz) Supports 1, 2, or 4 Lanes;
 1 Low speed video output—for video display on HDTV or other external display device;
  Noticeable latency is acceptable on HDTV display;
  HDMI/DVI.

The following table (Table I) lists various exemplary embodiments of processing unit 4:

TABLE I

|  | NI FlexRIO | NI Frame Grabber | Lattice HDR-60 | Lattice Video Protocol PCIe Board |
| --- | --- | --- | --- | --- |
| Expansion Bus | 8 Gbit/sec transfer rate via PXI bus | 8 Gbit/sec transfer rate via PXI bus | 1 Gbit/sec transfer rate via TCP/IP | 10 Gbit/sec transfer rate via PCIe bus |

In Table I, NI FlexRIO and NI Frame Grabber are processing modules manufactured by National Instruments Corporation at 11500 N Mopac Expwy Austin, Tex. 78759-3504, and Lattice HDR-60 and Lattice Video Protocol PCIe Board are processing modules manufactured by Lattice Semiconductor Corporation at 5555 NE Moore Conn., Hillsboro, Oreg. 97124. CameraLink, GigE, Firewire, Nanovesta, SDI, and DVI are data transmission protocols and standards known in the art.

Figure 24:
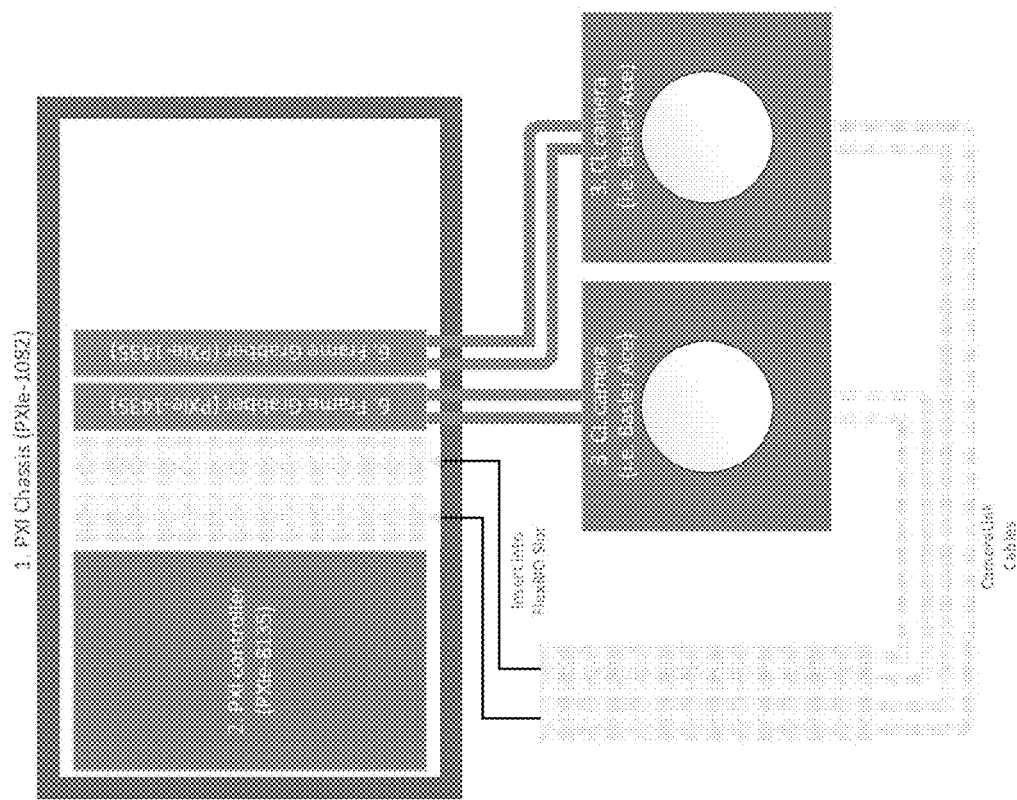
FIG. 24 illustrates an exemplary schematic diagram of a processing unit of FIG. 1, according to an embodiment.

FIG. 24 illustrates an embodiment of processing unit 4 using the NI Frame Grabber listed in Table I. In this embodiment, processing unit 4 may include two NI Frame Grabbers, each including an NI PXIe-1435 module and connected to a camera, such as the Ace series manufactured by Basler AG at An der Strusbek 60-62, 22926 Ahrensburg, Germany. The NI Frame Grabbers may be integrated in or inserted into a PXI chassis, such as an NI PXIe-1082. The PXI chassis may further include a PXI Controller, such as an NI PXIe-8135 and two NI PXIe-7962R for respective cameras. Each NI PXIe-7962R may include a CameraLink Module, such as an NI-1483, integrated in the FlexRIO slot thereon and coupled to the respective camera. In this embodiment, the processing of the video data is performed on a central processing unit (CPU). The PXI platform provides capabilities for further expansions. The Camera-Link connection provides a wide range of camera options and fast data transfer rates.

Figure 25:
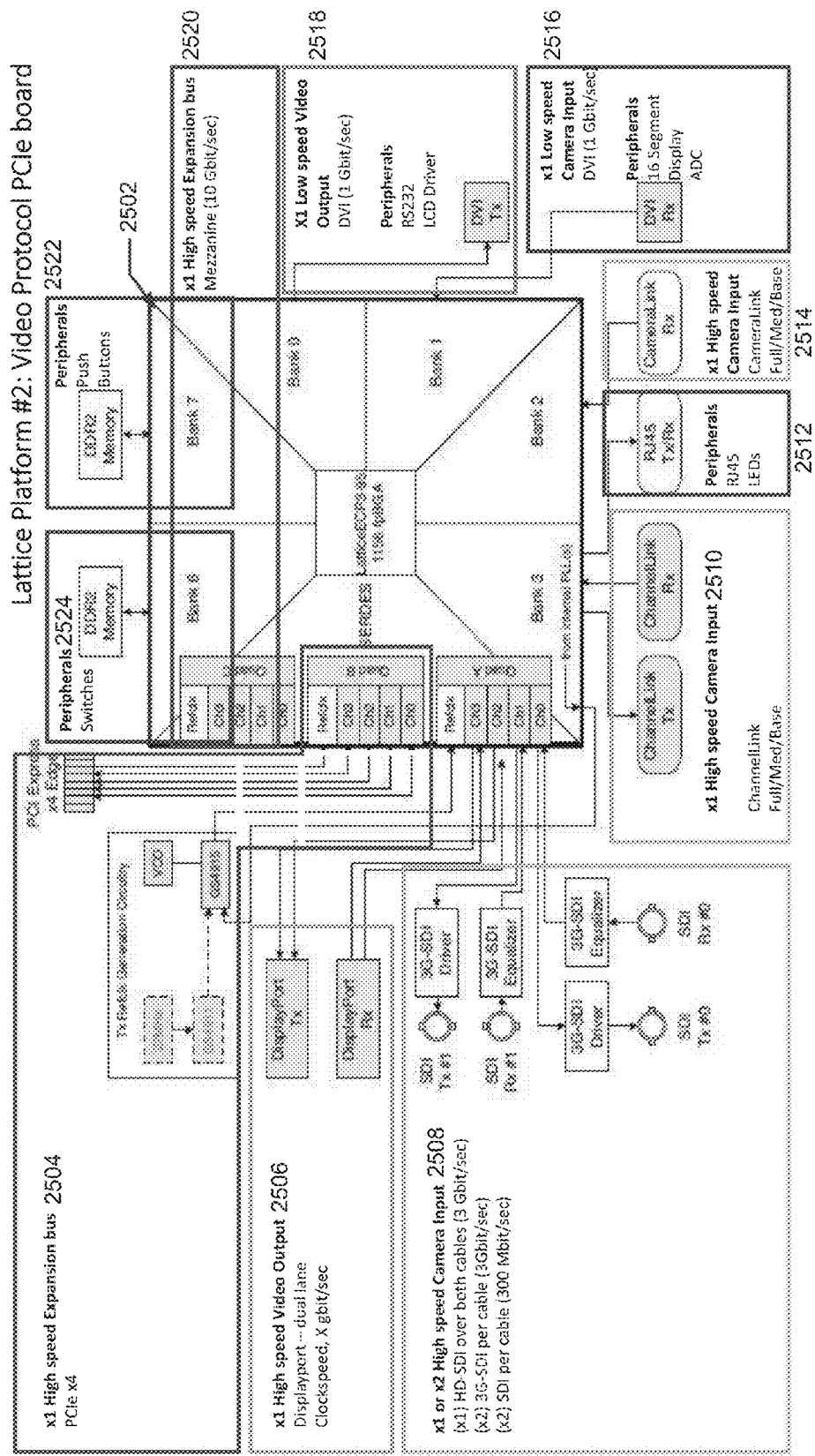
FIG. 25 illustrates an exemplary schematic diagram of the processing unit of FIG. 1, according to another embodiment.

FIG. 25 illustrates another embodiment of processing unit 4 using the Lattice Video Protocol PCIe Board listed in Table I above. The Lattice Video Protocol PCIe Board includes a central processing unit (CPU) 2502, such as a Lattice ECP3, and a plurality of processing modules. In one embodiment, the Lattice Video Protocol PCIe Board includes a high-speed expansion module 2504 including 4 PCIe expansion ports, a high-speed video output module 2506 to support Displayport interfaces, one or two high-speed camera input modules 2508 for receiving video data in, for example, HD-SDI format, 3G-SDI format, or SDI format, a high-speed camera input module 2510 to support ChannelLink interfaces, a peripheral module 2512 to support RJ45 or LED interfaces, a high-speed camera input module 2514 to support CameraLink interfaces, a low-speed camera input 2516 to receive video data in, for example, DVI format, a low-speed video output module 2518 to output data in, for example, the DBI format, an high-speed expansion bus 2520 to support additional mezzanine expansion cards for functional expansions, a peripheral module 2522 to support push buttons, and a peripheral module 2524 to support switches. Central processing unit 2502 may include a plurality of banks (e.g., Bank 0, Bank 1, Bank 2, etc.) to interface with the processing components.

Figure 26:
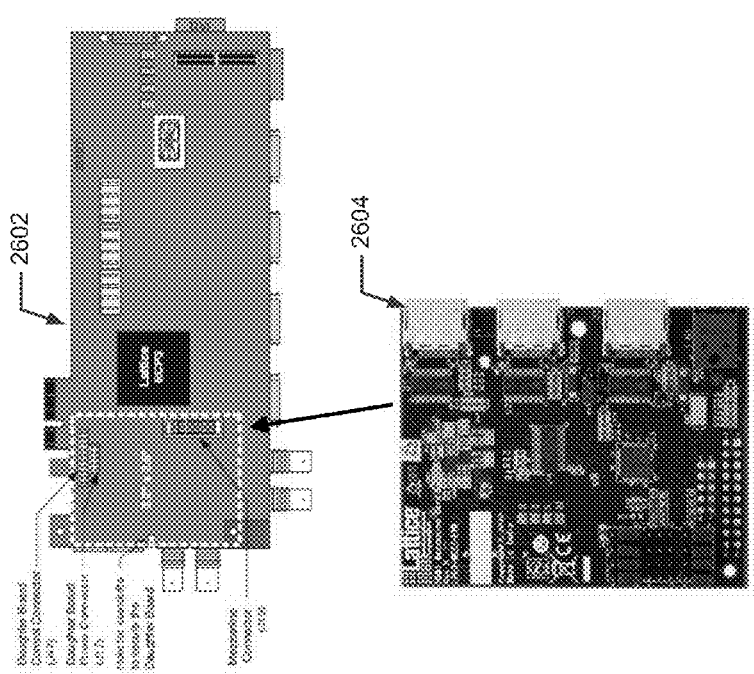
FIG. 26 illustrates an exemplary mezzanine expansion card for additional video inputs and outputs, according to an embodiment.

FIG. 26 illustrates an embodiment of a mezzanine expansion card for providing additional DVI inputs and outputs in the Lattice Video Protocol PCIe Board of processing unit 4 described above. In this embodiment, processing unit 4 may include a Lattice Video Protocol PCIe Board 2602 similar to that described above to process video data from image source 3 and generate the overlaid images for the display device. Lattice Video Protocol PCIe Board 2602 may include a Mezzanine Expansion Daughter Board 2604 to provide the additional inputs and outputs for further functional expansion. Mezzanine Expansion Daughter Board 2604 may be coupled to Lattice Video Protocol PCIe Board 2602 through a daughter board control connector (e.g., a J47 connector), a daughter board power connector (e.g., a J17 connector), and a mezzanine connector (e.g., a J19 connector). Lattice Video Protocol PCIe Board 2602 may further include one or more holes to secure Mezzanine Expansion Daughter Board 2604 thereon.

Figure 27:
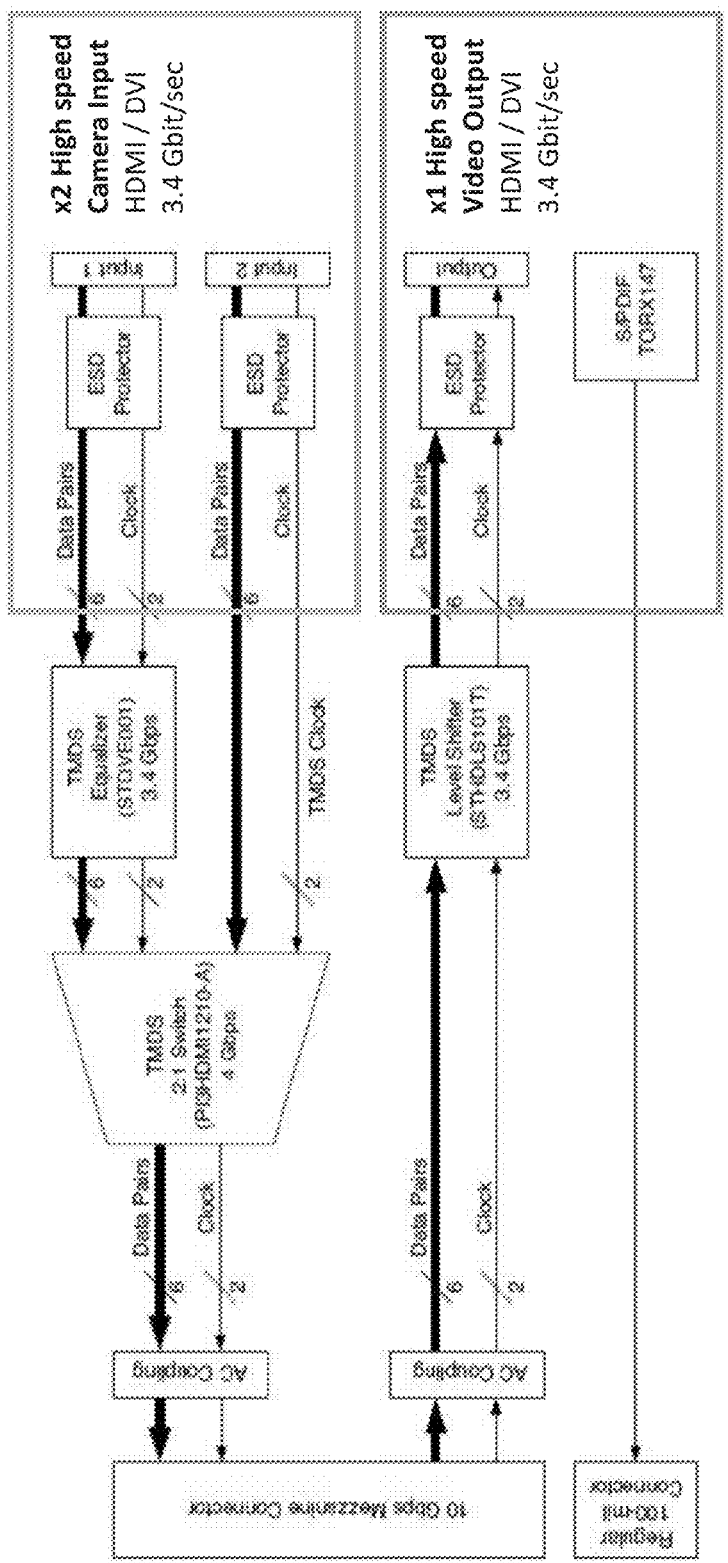
FIG. 27 illustrates an exemplary circuit diagram for the mezzanine expansion card of FIG. 26, according to an embodiment.

FIG. 27 illustrates a circuit 2700 for Mezzanine Expansion Daughter Board 2604 described above, according to an embodiment. In this embodiment, circuit 2700 may include two high-speed camera inputs for receiving inputs signals carrying the video data from image source 3. Camera inputs may receive inputs signals in HDMI format or DVI format. Circuit 2700 may also include a high-speed video output for transmitting output signals carrying the overlaid images generated by processing unit 4. The camera inputs and video output may support a transfer rate of 3.4 gigabits per second. The camera inputs and video output may be coupled to the mezzanine connector through various AC coupling, switch, shifter, and/or equalizer and communicate with the central processing unit (e.g., the Lattice ECP3 processor) on the Lattice Video Protocol PCIe Board through the mezzanine connector. The mezzanine connector may support a transfer rate of 10 Gbps.

Figure 28:
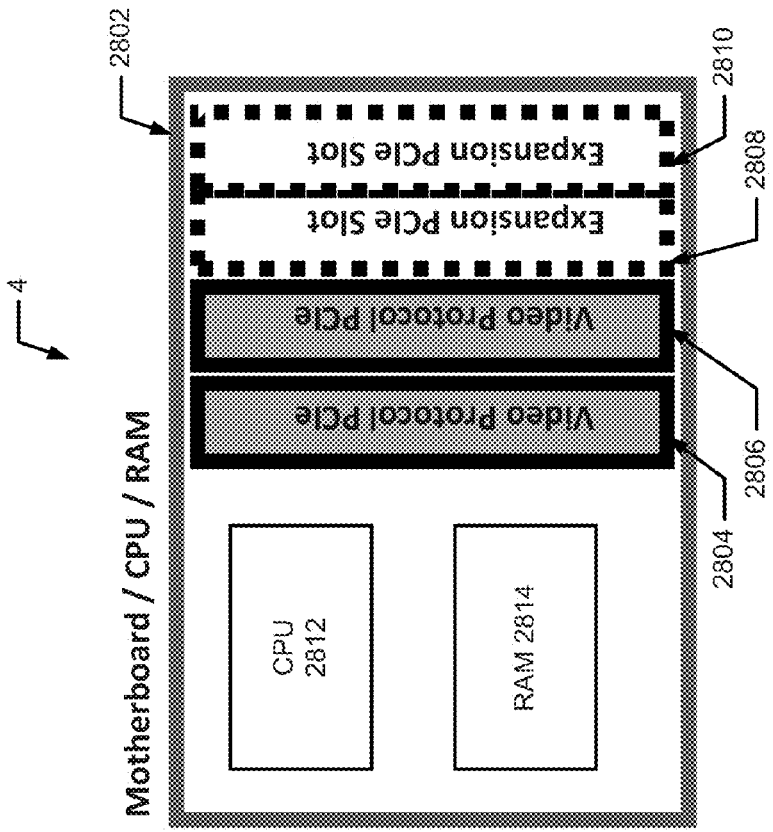
FIG. 28 illustrates a hardware implementation of the processing unit of FIG. 1, according to an embodiment.

FIG. 28 illustrates a hardware implementation of processing unit 4 based on the Lattice Video Protocol PCIe Board 2602 described above, according to an embodiment. In this embodiment, processing unit 4 may include a motherboard 2802 with a CPU 2812 and a random access memory (RAM) 2814 disposed thereon. CPU 2812 receives instructions from RAM 2814 for processing data and control operations of processing unit 4. Processing unit 4 may further include Lattice Video Protocol PCIe Boards 2804 and 2806 coupled to respective expansion PCIe slots disposed on motherboard 2802. Lattice Video Protocol PCIe Boards 2804 and 2806 may be connected to image source 3 and receive video data from respective cameras 3a and 3b. Lattice Video Protocol PCIe Boards 2804 and 2806 may further process the video data for the left and right video channels, respectively, to generate the overlaid images and transmit the overlaid images to the display device to generate the stereoscopic images to be displayed to the surgeon. Motherboard 2802 may include additional expansion PCIe slots 2808 and 2810 for further functional expansions. TCP/IP driver for network communication may be provided either by RJ45 on Video Protocol PCIe Boards 2804 and 2806 or by motherboard 2802. An advantage of using the motherboard is that the TCP/IP driver may be written in Labview or other high level language and data is transferred through PCIe. In a further embodiment, processing unit 4 may be programmed using the LabVIEW Development Suite, the Lattice Diamond Suite VHDL/Verilog, or the Lattice Diamone Suite MICO8.

Figure 29:
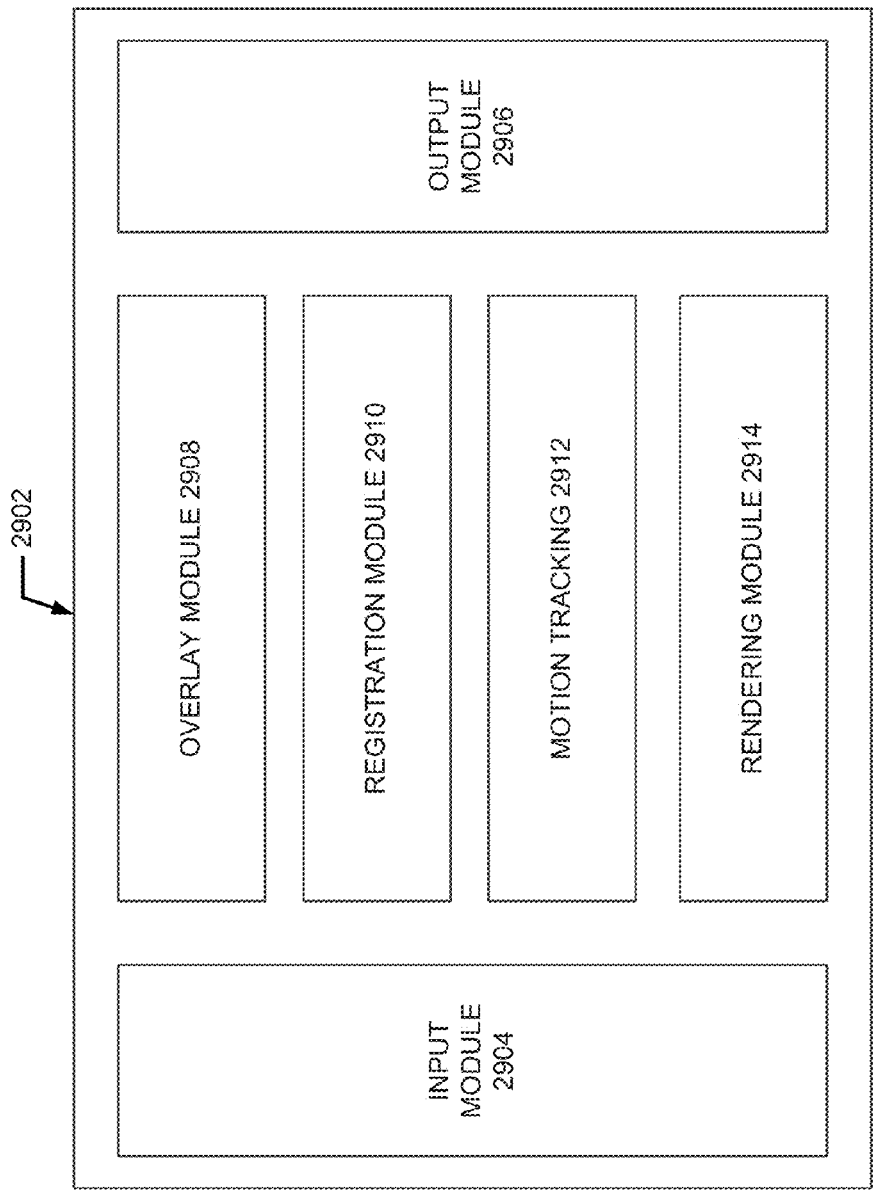
FIG. 29 illustrates a schematic diagram of a computer program implemented on the processing unit of FIG. 1, according to an embodiment.

FIG. 29 is a block diagram of a software program 2902 implemented on processing unit 4 for assisting a surgeon in a surgical procedure, according to an embodiment. Program 2902 may be stored in non-transitory computer-readable media in or coupled to processing unit 4 in the form of computer instructions to be executed by processing unit 4 for carrying out the image processing techniques disclosed herein. Program 2902 includes an input module 2904, an output module 2906, an overlay module 2908, a registration module 2910, a motion tracking module 2912, and a rendering module 2914.

Input module 2904 is configured to receive video data representing patient images from image source 3. Input module 2904 may also receive the external data from external data source 5. Input module 2904 may also receive the motion signals from the display device representing the motions of the surgeon detected by the motion sensor disposed in the display device. Input module 2904 may also receive user inputs from user input devices 11 for controlling and configuring processing unit 4.

Output module 2906 is configured to output digital signals representing overlaid images to the display device for display to the surgeon. Output module 2906 may also output the signals to other display devices, such as external monitor 9 (FIG. 1). Output module 2906 may also output digital signals representing the overlaid images with other surgical parameters to external computer system 8 for further processing and storage.

Overlay module 2908 is configured to merge the video data with the external data and generate the overlaid images, including a representation of the external data superimposed on a presentation of the patient images. Overlay module 2908 may also generate representations of other image features, such as the circular coordinate system corresponding to the patient's cornea or limbus or the warning for alerting the surgeon to abnormalities, and superimpose these image features on the patient images.

Registration module 2910 is configured to identify marks on the patient and register the patient images during a surgical procedure. The marks for registration may be artificial marks placed on the patient prior to the surgery or anatomical marks, such as blood vessels, iris patterns, or any other anatomical features that are sufficiently prominent to provide identification and registration. Registration module 2910 may register the patient images obtained at different time by image sources 3 when the image features change due to motions of the patient or the surgeon. Registration module 2910 ay also register the patient images to image data of other modalities, such as CT, MRI, X-Ray, Ultrasound, etc. Registration module 2910 may update the overlaid images based on the registration by, for example, changing the location of the representation of the external data.

Tracking module 2912 is configured to detect movement of the surgeon and/or patient during the surgery. Tracking module 2912 may detect movement of the surgeon based on the motion signals from motion sensor. Tracking module 2912 may detect rotational translational movement of the surgeon and adjust the region of interest displayed by the display device. Tracking module 2912 may move the region of interest within the field of view of the image source 3 according to the movement of the surgeon. Thus, tracking module 2912 allows the surgeon to view patient images within a relatively large field of view through the display device while also viewing in detail a relatively small region of interest.

Rendering module 2912 is configured to generate features in the overlaid images according to various rendering parameters. For example, rendering module 2912 may generate the virtual gauge, the virtual panel, the textual messages, the graphical elements, and other image elements included in the overlaid images. Rendering module 2912 may determine rendering parameters, such as shape, size, color, shading, culling, perspective, etc., for each image elements. Rendering module 2912 may also adjust the rendering parameters during the surgery according to user inputs or the patient images. For example, rendering module 2912 may hide/show an image element, rendering the image element in a semi-transparent mode, zoom in/out the image element according to the zooming of the patient images, etc. Rendering module 2912 may further adjust rendering of the patient images. For example, rendering module 2912 may perform image processing on patient images to enhance features included therein. Rendering module 2912 may perform filtering, sharpening, color-coding, or any other image processing on the patient images to assist the viewing of the anatomical features by the surgeon.

Systems and methods embodying principles of the present disclosure may provide a surgeon with the benefit of having real-time data superimposed over the visual surgical field. Additionally, it may give the surgeon the ability to perform camera-based operations with three-dimensional visualization, as compared to current two-dimensional technologies.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents that all fall within the scope of the embodiments described herein. Accordingly, the embodiments described herein are not to be considered as limited by the foregoing description.

What is claimed is:

1. A surgical guidance system for assisting a surgeon in a surgical procedure performed on a patient, the system comprising:
an image acquisition device configured to generate substantially real-time digital video data representing patient images of an eye of the patient;
a processor coupled to the image acquisition device and configured to:
receive the digital video data from the image acquisition device;
receive external data from an external data source;
generate composite digital image data based on the digital video data and the external data;
determine an expected result of the surgical procedure based on the external data; and
incorporate the expected result into the composite digital image data; and
a display device coupled to the processor, the display device being configured to display, to the surgeon from the composite digital image data, overlaid images including procedural prompts according to the patient images and the external data, wherein the display device includes first and second display modules configured to display the first and second patient images respectively to left and right eyes of the surgeon;
wherein the overlaid images further include the expected result superimposed on the patient images of the eye of the patient, the expected result indicates a surgical incision in the eye, and the surgical incision is a capsulorhexis incision.

2. The system of claim 1, wherein the image acquisition device comprises first and second cameras generating video data representing patient images at first and second viewing angles, respectively.

3. The system of claim 1, wherein the first and second patient images data form a stereoscopic representation of a portion of the patient images.

4. The system of claim 1, wherein the processor is further configured to generate prompts indicating steps of the surgical procedure for the surgeon to perform.

5. The system of claim 4, wherein the prompts comprise text data and image data.

6. The system of claim 5, wherein the image data comprise one or more image icons corresponding to the text data.

7. The system of claim 1, wherein the overlaid images include a first region representing the eye of the patient and a second region representing the external data.

8. The system of claim 7, wherein:
the first region is at a central portion of the overlaid images; and
second region is at a peripheral portion of the overlaid images.

9. The system of claim 7, wherein the first region and the second region partially overlap.

10. The system of claim 1, wherein:
the external data include anatomical measurements of the eye of the patient; and
the overlaid images include a first representation of the eye of the patient and a second representation of the anatomical measurement superimposed on the first representation.

11. The system of claim 10, wherein the processor is further configured to align the video data with the anatomical measurements.

12. The system of claim 11, wherein the processor is further configured to:
detect one or more anatomical features of the eye of the patient in the digital video data;
register the detected anatomical features to the anatomical measurements;
generate the prompts based on the registration; and
incorporate the prompts into the composite digital image data.

13. The system of claim 10, wherein the external data include at least one of ultrasound power, vacuum pressure, aspiration, or bottle height.

14. The system of claim 10, wherein the external data include a pre-operative image of the eye of the patient.

15. The system of claim 14, wherein the pre-operative image includes at least one of an MRI image, a CT image, an OTC image, an X-Ray image, or an fluorescein angiography image.

16. The system of claim 14, wherein the pre-operative image indicates one or more marks placed on the eye of the patient.

17. The system of claim 16, wherein the processor is further configured to register the digital video data to the pre-operative image based on the one or more marks.

18. The system of claim 10, wherein the processor is further configured to generate the anatomical measurements based on the external data.

19. The system of claim 1, wherein:
the overlaid images include a graphical representation of the eye of the patient; and
the graphical representation of the expected result indicates a surgical incision expected in the eye.

20. The system of claim 19, wherein the graphical representation of the expected result indicate an expected limbic incision.

21. The system of claim 19, wherein the processor is further configured to:
track anatomical features of the eye of the patient based on the image data;
compare the anatomical features with the expected surgical incision; and
display the prompts based on the comparison.

22. The system of claim 21, wherein the anatomical features include at least one of a blood vessel pattern or an iris pattern of the eye.

23. The system of claim 19, wherein the graphical representation of an expected result indicates an expected orientation of an axis of an artificial lens.

24. The system of claim 23, wherein the processor is further configured to determine an alignment of the expected orientation with a current axis of the artificial lens.

25. A medical data visualization system, comprising:
an image acquisition device configured to generate substantially real-time video data representing patient images of a patient corresponding to a field of view;
a processor coupled to the image acquisition device and configured to:
receive the video data from the image acquisition device;
receive external data from an external data source; and
generate composite digital image data based on the video data and the external data; and
a display device coupled to the processor, the display device being configured to display overlaid images including:
a portion of the patient image corresponding to a region of interest; and
a graphical representation of the external data,
wherein the region of interest is smaller than the field of view and a magnification of the region of interest is greater than the magnification of the field of view.

26. The system of claim 25, wherein the display device is further configured to adjust the region of interest within the field of view.

27. The system of claim 26, wherein the display device is an eyewear device configured to be worn by the surgeon.

28. The system of claim 27, wherein:
the system further comprises a motion sensor configured to generate a motion signal conveying a head motion of the surgeon; and
the processor is further configured to adjust the region of interest according to the motion signal.

29. The system of claim 28, wherein the motion sensor is disposed in the eyewear device.

30. The system of claim 28, wherein:
the motion sensor is configured to detect a rotation of a head portion of the surgeon.

31. A computer system for assisting a surgeon in a surgical procedure performed on a
patient, the computer system comprising:
an input module configured to receive:
from an image acquisition device, substantially real-time digital video data representing patient images of an eye of the patient; and
external data;
a processing module configured to generate composite digital image data based on the digital video data and the external data; and
an output module configured to transmit the composite digital image data to a display device for display of overlaid images including procedural prompts corresponding to the patient images and the external data, wherein the display device includes first and second display modules configured to display the first and second patient images respectively to left and right eyes of the surgeon.

32. A display device for assisting a surgeon in a surgical procedure performed on a patient, the device comprising:
a housing configured to be worn by the surgeon;
a receiving module; and
a display module, wherein:
the receiving module is configured to receive composite digital image data from a processor including substantially real-time digital video data and external data, the digital video data representing patient images of an eye of the patient, wherein the digital video data includes first and second images of an eye of the patient;
the display module is configured to display, to the surgeon from the composite digital image data, overlaid images including procedural prompts corresponding to the patient images and the external data; and
wherein the display module includes first and second display modules configured to display the first and second patient images respectively to left and right eyes of the surgeon.

33. The device of claim 32, further comprising a motion sensor disposed within the housing and configured to detect a motion of the surgeon, wherein the display module is further configured adjust the overlaid images according to the detected motion of the surgeon.

34. A method for assisting a surgeon in a surgical procedure performed on a patient, the method comprising:
receiving substantially real-time digital video data representing patient images of an eye of the patient, wherein the substantially real-time digital video data includes first and second images of an eye of the patient;
receiving external data from an external data source;
generating composite digital image data based on the digital video data and the external data; and
transmitting the composite digital image data to a display device for display of overlaid images from the composite digital image data, the overlaid images including procedural prompts for the surgical procedure corresponding to the patient images and the external data, wherein the display device includes first and second display modules configured to display the first and second patient images respectively to left and right eyes of the surgeon.

35. The method of claim 34, wherein the overlaid images include a virtual gauge comprising the prompts.

36. The method of claim 35, wherein the virtual gauge has a shape conformed to a contour of the eye of the patient.

37. The method of claim 36, wherein the virtual gauge has one of a circular shape or a fan shape.

38. A non-transitory computer-readable medium comprising instructions, which, when executed by one or more processors, cause the processors to perform a method for assisting a surgeon in a surgical procedure performed on a patient, the method comprising:
receiving substantially real-time digital video data representing patient images of an eye of the patient, wherein the substantially real-time digital video data includes first and second images of an eye of the patient;
receiving external data from an external data source;
generating composite digital image data based on the digital video data and the external data; and
transmitting the composite digital image data to a display device, for display of overlaid images from the composite digital image data, the overlaid images including procedural prompts for the surgical procedure corresponding to the patient images and the external data, wherein the display device includes first and second display modules configured to display the first and second patient images respectively to left and right eyes of the surgeon.

* * * * *